(12) United States Patent
Yamaguchi et al.

(10) Patent No.: US 11,856,952 B2
(45) Date of Patent: Jan. 2, 2024

(54) MICROBIAL OIL, PRODUCTION METHOD FOR MICROBIAL OIL, CONCENTRATED MICROBIAL OIL, AND PRODUCTION METHOD FOR CONCENTRATED MICROBIAL OIL

(71) Applicant: NIPPON SUISAN KAISHA, LTD., Tokyo (JP)

(72) Inventors: Hideaki Yamaguchi, Tokyo (JP); Yuhei Kosuge, Tokyo (JP); Rie Ikeda, Tokyo (JP); Nobushige Doisaki, Tokyo (JP); Seizo Sato, Tokyo (JP)

(73) Assignee: NIPPON SUISAN KAISHA, LTD., Tokyo (JP)

( * ) Notice: Subject to any disclaimer, the term of this patent is extended or adjusted under 35 U.S.C. 154(b) by 0 days.

(21) Appl. No.: 17/720,595

(22) Filed: Apr. 14, 2022

(65) Prior Publication Data

US 2022/0248671 A1    Aug. 11, 2022

Related U.S. Application Data

(62) Division of application No. 15/101,436, filed as application No. PCT/JP2014/082167 on Dec. 4, 2014, now Pat. No. 11,330,817.

(30) Foreign Application Priority Data

Dec. 4, 2013 (JP) .................................. 2013-251401

(51) Int. Cl.

| | | |
|---|---|---|
| *A01N 37/06* | (2006.01) | |
| *A61K 31/202* | (2006.01) | |
| *C11B 1/02* | (2006.01) | |
| *C11B 3/12* | (2006.01) | |
| *C11C 1/00* | (2006.01) | |
| *A61K 8/36* | (2006.01) | |
| *A61Q 19/00* | (2006.01) | |
| *A23L 33/115* | (2016.01) | |
| *C12N 1/28* | (2006.01) | |
| *C12P 7/6427* | (2022.01) | |
| *C12P 7/6436* | (2022.01) | |
| *C12P 7/6463* | (2022.01) | |
| *A23D 9/013* | (2006.01) | |
| *A23D 9/02* | (2006.01) | |
| *C11B 3/10* | (2006.01) | |
| *C11C 3/10* | (2006.01) | |
| *A23K 20/158* | (2016.01) | |
| *A61K 8/9706* | (2017.01) | |
| *A61K 8/9728* | (2017.01) | |
| *A61K 8/99* | (2017.01) | |
| *A61K 36/06* | (2006.01) | |

(52) U.S. Cl.
CPC ............ *A01N 37/06* (2013.01); *A23D 9/013* (2013.01); *A23D 9/02* (2013.01); *A23K 20/158* (2016.05); *A23L 33/115* (2016.08); *A61K 8/361* (2013.01); *A61K 8/9706* (2017.08); *A61K 8/9728* (2017.08); *A61K 8/99* (2013.01); *A61K 31/202* (2013.01); *A61K 36/06* (2013.01); *A61Q 19/00* (2013.01); *C11B 1/025* (2013.01); *C11B 3/10* (2013.01); *C11B 3/12* (2013.01); *C11C 1/005* (2013.01); *C11C 3/10* (2013.01); *C12N 1/28* (2013.01); *C12P 7/6427* (2013.01); *C12P 7/6436* (2013.01); *C12P 7/6463* (2013.01)

(58) Field of Classification Search
None
See application file for complete search history.

(56) References Cited

U.S. PATENT DOCUMENTS

| | | | |
|---|---|---|---|
| 4,776,984 A | 10/1988 | Traitler et al. | |
| 4,950,430 A * | 8/1990 | Chen .................. | B01J 19/32 |
| | | | 261/112.2 |

(Continued)

FOREIGN PATENT DOCUMENTS

| | | |
|---|---|---|
| CA | 2873160 A1 | 11/2013 |
| CN | 1222564 A | 7/1999 |

(Continued)

OTHER PUBLICATIONS

Li, Zu-Yi, et al. "Process for production of arachidonic acid concentrate by a strain of Mortierella alpina." The Canadian Journal of Chemical Engineering 73.1 (1995): 135-139. (Year: 1995).*
Shimada, Yuji, Akio Sugihara, and Yoshio Tominaga. "Enzymatic purification of polyunsaturated fatty acids." Journal of bioscience and bioengineering 91.6 (2001): 529-538. (Year: 2001).*
Zhu, M., P. P. Zhou, and L. J. Yu. "Extraction of lipids from Mortierella alpina and enrichment of arachidonic acid from the fungal lipids." Bioresource technology 84.1 (2002): 93-95. (Year: 2002).*
Streekstra, Hugo. "Arachidonic acid: fermentative production by Mortierella fungi." Single cell oils. AOCS Press, 2010. 97-114. (Year: 2010).*

(Continued)

*Primary Examiner* — Bethany P Barham
*Assistant Examiner* — Peter Anthopolos
(74) *Attorney, Agent, or Firm* — Banner & Witcoff, LTD

(57) ABSTRACT

A microbial oil comprising: a specific amount of at least one polyunsaturated fatty acid having at least 20 carbon atoms in fatty acid alkyl ester form and/or in free fatty acid form; and specific amount of thermally-produced fatty acid having from 16 to 22 carbon atoms in a fatty acid alkyl ester form and/or a free fatty acid form. A production method thereof comprising: providing a starting oil containing at least one polyunsaturated fatty acid having at least 20 carbon atoms in an alkyl ester form and/or a free fatty acid form obtained from microbial biomass; performing a rectification of the starting oil under specific conditions; and obtaining the aforementioned microbial oil. A concentrated microbial oil obtained using the production method described above, and a production method thereof. An agent for treating or preventing an inflammatory disease comprising the microbial oil or the concentrated microbial oil.

20 Claims, No Drawings

(56) References Cited

U.S. PATENT DOCUMENTS

| | | | |
|---|---|---|---|
| 5,145,686 A | 9/1992 | Horrobin et al. | |
| 5,204,250 A * | 4/1993 | Shinmen | C12P 7/6472 435/244 |
| 5,215,630 A | 6/1993 | Hata et al. | |
| 5,376,541 A | 12/1994 | Kawashima et al. | |
| 5,668,174 A | 9/1997 | Kawagishi et al. | |
| 5,840,944 A | 11/1998 | Furihata et al. | |
| 5,847,000 A | 12/1998 | Horrobin et al. | |
| 5,914,347 A | 6/1999 | Grinda | |
| 5,945,318 A | 8/1999 | Breivik et al. | |
| 5,968,809 A | 10/1999 | Knutzon et al. | |
| 5,972,664 A | 10/1999 | Knutzon et al. | |
| 6,117,905 A * | 9/2000 | Higashiyama | A23L 33/12 514/560 |
| 6,177,470 B1 | 1/2001 | Horrobin et al. | |
| 6,479,544 B1 | 11/2002 | Horrobin | |
| 7,470,527 B2 * | 12/2008 | Streekstra | C11B 1/10 426/601 |
| 7,718,698 B2 | 5/2010 | Breivik et al. | |
| 9,540,306 B2 | 1/2017 | Doisaki et al. | |
| 2001/0021522 A1 | 9/2001 | Kawashima et al. | |
| 2001/0025112 A1 | 9/2001 | Fujita et al. | |
| 2001/0042340 A1 | 11/2001 | Tateno et al. | |
| 2003/0166723 A1 | 9/2003 | Nakajima et al. | |
| 2004/0067574 A1 | 4/2004 | Bijl et al. | |
| 2004/0122246 A1 * | 6/2004 | Sparso | C11B 3/12 554/175 |
| 2005/0256326 A1 | 11/2005 | Breivik et al. | |
| 2005/0287651 A1 | 12/2005 | Akimoto et al. | |
| 2006/0110806 A1 | 5/2006 | Damude et al. | |
| 2008/0108699 A1 | 5/2008 | Tateishi et al. | |
| 2009/0036532 A1 | 2/2009 | Marciacq et al. | |
| 2010/0130610 A1 | 5/2010 | Keller et al. | |
| 2010/0167359 A1 | 7/2010 | Katano et al. | |
| 2010/0317622 A1 | 12/2010 | Kawashima et al. | |
| 2011/0130458 A1 | 6/2011 | Breivik et al. | |
| 2011/0263708 A1 | 10/2011 | Cohen et al. | |
| 2012/0142773 A1 | 6/2012 | Kelliher et al. | |
| 2012/0330043 A1 | 12/2012 | Kelliher et al. | |
| 2013/0046020 A1 | 2/2013 | Liang et al. | |
| 2013/0046106 A1 * | 2/2013 | Liang | B01D 3/12 554/175 |
| 2013/0292242 A1 | 11/2013 | Hietsch et al. | |
| 2014/0275251 A1 | 9/2014 | Takeo et al. | |
| 2015/0126760 A1 | 5/2015 | Doisaki et al. | |
| 2015/0252288 A1 | 9/2015 | Harata et al. | |
| 2016/0051504 A1 | 2/2016 | Takeo et al. | |
| 2017/0081272 A1 | 3/2017 | Doisaki et al. | |
| 2017/0252315 A1 | 9/2017 | Doisaki et al. | |

FOREIGN PATENT DOCUMENTS

| | | |
|---|---|---|
| CN | 1252099 A | 5/2000 |
| CN | 101560440 A | 10/2009 |
| CN | 103804171 A | 5/2014 |
| DE | 20 2008 006 708 U1 | 9/2008 |
| EP | 0 085 579 A2 | 8/1983 |
| EP | 0 173 478 A1 | 3/1986 |
| EP | 0 454 102 A2 | 10/1991 |
| EP | 460917 A2 | 12/1991 |
| EP | 0 611 569 A1 | 8/1994 |
| EP | 0 675 120 A2 | 10/1995 |
| EP | 2438819 A1 | 4/2012 |
| GB | 2 327 347 A | 1/1999 |
| JP | S57149400 A | 9/1982 |
| JP | S5888339 A | 5/1983 |
| JP | S58208217 A | 12/1983 |
| JP | S60208940 A | 10/1985 |
| JP | H04041457 A | 2/1992 |
| JP | H05-91887 A | 4/1993 |
| JP | H05222392 A | 8/1993 |
| JP | H0633088 A | 2/1994 |
| JP | H07-233062 A | 9/1995 |
| JP | H08100191 A | 4/1996 |
| JP | H09510091 A | 10/1997 |
| JP | H10095744 A | 4/1998 |
| JP | H10-218731 A | 8/1998 |
| JP | H10-508287 A | 8/1998 |
| JP | 10310551 A * | 11/1998 |
| JP | H10-310551 A | 11/1998 |
| JP | H11-209785 A | 8/1999 |
| JP | H11-209786 A | 8/1999 |
| JP | 2001302584 A | 10/2001 |
| JP | 2001303089 A | 10/2001 |
| JP | 2002-047176 A | 2/2002 |
| JP | 3354581 B2 | 12/2002 |
| JP | 2004-504849 A | 2/2004 |
| JP | 2006-219454 A | 8/2006 |
| JP | 2007-089522 A | 4/2007 |
| JP | 3905538 B2 | 4/2007 |
| JP | 2010-526896 A | 8/2010 |
| JP | 2010-532418 A | 10/2010 |
| JP | 2011522913 A | 8/2011 |
| JP | 2014-510166 A | 4/2014 |
| JP | 2014510165 A | 4/2014 |
| WO | WO-2002/06430 A1 | 1/2002 |
| WO | WO-2005/083101 A1 | 9/2005 |
| WO | WO-2006/085687 A1 | 8/2006 |
| WO | WO-2009/006317 A1 | 1/2009 |
| WO | WO-2010/125340 A1 | 11/2010 |
| WO | WO-2011/080503 A2 | 7/2011 |
| WO | WO-2011/154947 A2 | 12/2011 |
| WO | WO-2011161702 A1 * | 12/2011 | C11B 3/003 |
| WO | WO-2012/109539 A1 | 8/2012 |
| WO | WO-2012-109563 A1 | 8/2012 |
| WO | WO-2012/153832 A1 | 11/2012 |
| WO | WO-2013/082265 A1 | 6/2013 |
| WO | WO-2013/172346 A1 | 11/2013 |
| WO | WO-2014/054435 A1 | 4/2014 |
| WO | WO-2014/068056 A1 | 5/2014 |
| WO | WO-2015/083843 A2 | 6/2015 |

OTHER PUBLICATIONS

Ratledge, Colin, et al. "Downstream processing, extraction, and purification of single cell oils." Single cell oils. AOCS Press, 2010. 179-197. (Year: 2010).*

Ji, Xiao-Jun, et al. "Fungal arachidonic acid-rich oil: research, development and industrialization." Critical reviews in biotechnology 34.3 (Apr. 30, 2013): 197-214. (Year: 2013).*

Mark G. Obukowicz, et al., "Novel, Selective Δ6 or Δ5 Fatty Acid Desaturase Inhibitors as Antiinflammatory Agents in Mice," J. Pharm Exp. Ther., vol. 287, No. 1 (1998) pp. 157-166.

International Search Report dated Mar. 10, 2015 for PCT/JP2014/082167.

Written Opinion dated Mar. 10, 2015 for PCT/JP2014/082167.

International Preliminary Report on Patentability (including PCT/ISA/237) dated Jun. 7, 2016 for PCT/JP2014/082167.

English translation of Written Opinion [PCT/ISA/237] dated Mar. 10, 2015 for PCT/JP2014/082167.

A. Anstey, et al., "Topical evening primrose oil as treatment for atopic eczema," Journal of Dermatological Treatment (1990) 1, pp. 199-201.

N.L. Morse, et al., "A Meta-Analysis of Randomized, Placebo-Controlled Clinical Trials of Efamol® Evening Primrose Oil in Atopic Eczema. Where Do We Go from Here in Light of More Recent Discoveries?," Current Pharmaceutical Biotechnology, 2006, 7, pp. 503-524.

Extended European Search Report corresponding to Application No. 12781963.9-1460/2708230 PCT/JP2012062114; dated Nov. 4, 2014.

International Search Report for International Application No. PCT/JP2012/062114; dated Jun. 12, 2012, with English Translation.

United States Non Final Office Action corresponding to U.S. Appl. No. 14/117,330, dated Mar. 6, 2015.

JOCS Standard Methods for the Analysis of Fats, Oils and Related Materials, Fatty Acid Composition (FID Isothermal Gas Chromatography), 2013 Edition, 2.4.2.1-2013.

(56) References Cited

OTHER PUBLICATIONS

JOCS Standard Methods for the Analysis of Fats, Oils and Related Materials, (FID Temperature Programmed Gas Chromatography), 2013 Edition, 2.4.2.2-2013.
JOCS Standard Methods for the Analaysis of Fats, Oils and Related Materials, Melting Point (Clear Point), 2013 Edition, 3.2.2.1-2013.
J. Hirsch et al., "The Separation of Complex Lipide Mixtures by the Use of Silicic Acid Chromatography", Journal of Biological Chemistry, 1958, 233:311-320.
F. Gunstone et al., "Chromatographic analysis of lipids", The Lipid Handbook with CD-ROM, Third Edition, CRC Press Taylor & Francis Group, 2007, p. 438-p. 439.
R.C. Wijesundera et al., "Eicosapentaenoic Acid Geometrical Isomer Artifacts in Heated Fish Oil Esters", Journal of the American Oil Chemists' Society, 1989, vol. 66, No. 12, pp. 1822-1830.
EP Application 14868372.5—Extended European Search Report dated Jul. 14, 2017.
Australian Application 2014358145—Official Communication dated Aug. 30, 2017.
Office Action dated Apr. 19, 2018 issued in corresponding EP Application No. 14868372.5.
Examination Report No. 2 dated Apr. 11, 2018 in corresponding AU Application No. 2014358145.
Bimbo, Anthony P., "Guidelines for Characterizing Food-Grade Fish Oil", INFORM 9 (5), pp. 473-483 (1998).
Breivik, H., et al., Preparation of Highly Purified Concentrates of Eicosapentaenoic acid and Docosahexaenoic acid, JAOCS, vol. 74, No. 11 (1997), pp. 1425-1429.
Breivik, Harald et al., "Removal of Organic Environmental Pollutants from Fish Oil by Short-path distillation", Lipid Technology, vol. 17, No. 3 (2005), pp. 55-58.
Cmolik, Jiri, et al. "Physical Refining of Edible Oils", Eur. J. Lipid Sci. Technol., 102 (2000), pp. 472-486.
Fournier, Veronique et al., "Thermal degradation of long-chain polyunsaturated fatty acids during deodorization of fish oil", Eur. J. Lipid Sci. Technol., vol. 108 (2006), pp. 33-42.
K. Julshamn et al., "Removal of DDT and Its Metabolites From Fish Oils by Molecular Distillation", Fiskeridirektoratets Skrifter Serie Teknologiske Undersokelser, vol. 5, No. 15 (1973), 10 pages.
Svein A. Mjos et al., "Geometrical isomerization of eicosapentaenoic and docosahexaenoic acid at high temperatures," European Journal of Lipid Science and Technology 108 (2006), pp. 589-597.
Shahidi, Fereidoon, et al., Chemistry of Fatty acids, Bailey's Industrial Oll and Fat Products, vol. 1 (2005), 17 pages.
R.C. Wijesundera et al., "Eicosapentaenoic Acid Geometrical Isomer Artifacts in Heated Fish Oil Esters," JAOCS; vol. 66, No. 12 (Dec. 1989), pp. 1822-1830.
Yamamura, Ryuji, et al., "High Purification of Polyunsaturated Fatty Acids", Journal of Japan Oil Chemists' Society, vol. 47, No. 5 (1998), pp. 449-456 (with English translation).
Yushi, "Dioxin is reduced in large quantities by the SPD processing method that constitutes the core of Fine Chemical operation", Industrial Report, Nippon Suisan Kaisha, Ltd., vol. 62, No. 11 (2009), pp. 38-39 (with English translation).
International Search Report in PCT/JP2013/063425, dated Aug. 6, 2013.
International Search Report in PCT/JP2015/076380, dated Dec. 15, 2015.
Final Office Action in U.S. Appl. No. 14/400,652, dated Mar. 4, 2016.
Non Final Office Action in U.S. Appl. No. 14/400,652 dated Aug. 26, 2015.
Non Final Office Action in U.S. Appl. No. 15/366,522, dated Aug. 24, 2017.
Final Office Action in U.S. Appl. No. 15/366,522, dated Mar. 28, 2018.
Extended European Search Report in EP Appl. No. 13790465.2-1451/2851361, PCT/JP2013/063425, dated Nov. 30, 2015.
Australian Patent Office, Examination Report for Australian Patent Application No. 2018229460, dated Aug. 26, 2019.
The State Intellectual Property Office of the People's Republic of China, Second Office Action for Chinese Patent Application No. 201480066446.2, dated May 13, 2020.
Cermak, S., et al. (2012). Distillation of Natural Fatty Acids and Their Chemical Derivatives, Distillation—Advances from Modeling to Applications, Dr. Sina Zereshki (Ed.), InTech, available at: http://www.intechopen.com/books/distillation-advances-from-modeling-to-applications/distillation-of-natural-fatty-acids-and-their-chemical-derivatives.
Haeffner, E. W. (1970). Separation of the $C_{20}$ Unsaturated Fatty Acids from Rapeseed Oil by Countercurrent Distribution. Lipids, vol. 5, No. 5, pp. 489-491.
Jareonkitmongkol, S., et al., "A Novel Δ5-Desaturase-Defective Mutant of Mortierella alpina 1S-4 and Its Dihomo-γ-Linolenic Acid Productivity," Appl. Environ. Microbiol., 1993, 59(12): 4300-4304.
Australian Patent Office, Examination Report for Australian Patent Application No. 2018204707, dated Nov. 10, 2020.
Japan Patent Office, Notice of Reasons for Refusal for Japanese Patent Application No. 2019-160981, dispatched Mar. 2, 2021.
Ogawa, J., et al., "Functional lipid production by an oil-accumulating fungus Mortierella alpina," Microbiol. Cult. Coll., 2011, 27(1): 25-29. [Partial translation].
Non Final Office Action in U.S. Appl. No. 15/511,757, dated Jul. 19, 2017.
Kawashima et al., "Industrial Production of Dihomo-γ-linolenic Acid by a '5 Desaturase-defective Mutant of Mortierella alpina 1S-4 Fungus," Journal of the American Oil Chemists' Society, vol. 77, No. 11, pp. 1135-1139, 2000.

* cited by examiner

MICROBIAL OIL, PRODUCTION METHOD FOR MICROBIAL OIL, CONCENTRATED MICROBIAL OIL, AND PRODUCTION METHOD FOR CONCENTRATED MICROBIAL OIL

This application is a divisional of U.S. patent application Ser. No. 15/101,436, filed Jun. 3, 2016, which is the National Stage of International Application No. PCT/JP2014/082167, filed Dec. 4, 2014, and claims benefit of Japanese Application No. 2013-251401 filed on Dec. 4, 2013, the contents of each of which is incorporated herein by reference.

TECHNICAL FIELD

The present invention relates to microbial oil, production methods for microbial oil, concentrated microbial oil, and production methods for concentrated microbial oil.

BACKGROUND

Microbial oils contain long-chain polyunsaturated fatty acids having at least 20 carbon atoms such as eicosadienoic acid, dihomo-γ-linolenic acid (DGLA), eicosatetraenoic acid, arachidonic acid (ARA), eicosapentaenoic acid (EPA), docosatetraenoic acid, docosapentaenoic acid, and docosahexaenoic acid (DHA). Medicaments, health foods, cosmetics, and the like using these long-chain polyunsaturated fatty acids as functional ingredients have attracted attention, and further applications are being investigated. Accordingly, there has been a demand for the production of polyunsaturated fatty acids in large quantities and at high concentrations.

In addition to long-chain polyunsaturated fatty acids, microbial oils contain a wide variety of unique oily components such as short-chain fatty acids, saturated fatty acids, phospholipids, sterols, glycerides, ceramides, sphingolipids, terpenoids, flavonoids and tocopherols. These components sometimes demonstrate unique functions. For example, short-chain fatty acids may cause an odor characteristic to microbial oils, and this characteristic odor may be undesirable for expressing the functions required of specific long-chain polyunsaturated fatty acids. In a case in which specific long-chain polyunsaturated fatty acids contained in microbial oils are concentrated or purified, high-performance liquid chromatography, liquid-liquid distribution, urea adduction, or the like may be used.

For example, Patent Document 1 discloses a process for reducing the amount of sterols in a sterol-containing microbial oil composition by distilling a microbial oil obtained from a gene recombinant microbe producing linoleic acid, DGLA, DHA, EPA or the like at least once under short path distillation conditions.

Patent Document 2 discloses a process for the preparation of a deodorized stabilized food-grade oil containing a marine oil, the method comprising submitting the oil to counter-current steam distillation (CCSD) in a thin film column containing a structured packing and, if desired, adding an antioxidant.

RELATED ART DOCUMENT

Patent Documents

Patent Document 1: Japanese Patent Application Laid-Open (JP-A) No. 2014-510166
Patent Document 2: Japanese Patent Application Laid-Open (JP-A) No. 2010-526896

SUMMARY OF THE INVENTION

Problems to be Solved by the Invention

The purpose of conventional methods is to separate some specific components other than fatty acids and the specific fatty acids to be concentrated or purified, and with conventional methods, it has been difficult to concentrate or purify long-chain polyunsaturated fatty acids to be concentrated or purified to a high degree. In a case in which a microbial oil is used as a starting material, it is not possible to sufficiently concentrate or purify the target long-chain polyunsaturated fatty acids to be concentrated or purified, because of the effects of a wide variety of other components contained in the starting material. Although concentration or purification may also be performed by means of distillation technology, distillation technology for concentrating or purifying the target long-chain polyunsaturated fatty acids in a microbial oil has not yet been sufficiently established.

The object of the present invention is to provide a microbial oil and a production method thereof useful for efficiently obtaining a purified microbial oil containing target polyunsaturated fatty acids at a high proportion, a concentrated microbial oil containing polyunsaturated fatty acids at a high content, a production method thereof, and respective applications of the microbial oil and the concentrated microbial oil.

Means for Solving the Problems

Each aspect of the present invention provides the following microbial oil, a production method for a microbial oil, a concentrated microbial oil, a production method for a concentrated microbial oil, and respective applications of the microbial oil and the concentrated microbial oil.

<1> A microbial oil comprising: at least one polyunsaturated fatty acid having at least 20 carbon atoms in fatty acid alkyl ester form and/or in free fatty acid form at a content of at least 50% by weight of the total weight of fatty acids in the oil; and thermally-produced fatty acid having from 16 to 22 carbon atoms at a content of at most 3.0% by weight of the total weight of fatty acids in the oil.

<2> The microbial oil according to <1>, wherein the content of the polyunsaturated fatty acid is from 80% by weight to 98% by weight of the total weight of fatty acids in the oil.

<3> The microbial oil according to <1> or <2>, wherein the content of the thermally-produced fatty acid is from 0.0001% by weight to 3.0% by weight of the total weight of fatty acids in the oil.

<4> The microbial oil according to any one of <1> to <3>, wherein the total content of saturated fatty acid having 22 carbon atoms and saturated fatty acid having 24 carbon atoms is at most 6.0% by weight of the total weight of fatty acids in the oil.

<5> The microbial oil according to any one of <1> to <4>, wherein the total content of saturated fatty acid having 22 carbon atoms and saturated fatty acid having 24 carbon atoms is at most 10/100 of the content of the polyunsaturated fatty acid.

<6> The microbial oil according to any one of <1> to <5>, wherein the content of saturated fatty acid having 24 carbon atoms is at most 3.0% by weight of the total weight of fatty acids in the oil.

<7> The microbial oil according to any one of <1> to <6>, wherein the content of saturated fatty acid having 24 carbon atoms is at most 4/100 of the content of the polyunsaturated fatty acid.

<8> The microbial oil according to any one of <1> to <7>, wherein the microbial oil has a content of other saturated or unsaturated fatty acid, having a partition number from 2 less than up to 2 greater than that of said polyunsaturated fatty acid and a number of carbon atoms different from the number of carbon atoms of said polyunsaturated fatty acid, of at most 10.0% by weight of the total weight of fatty acids in the oil, wherein the partition number used is an index related to separation in liquid chromatography and is determined from the number of carbon atoms and the number of double bonds of a fatty acid.

<9> The microbial oil according to <8>, wherein a content of the other saturated or unsaturated fatty acid is at most 15/100 of the content of the polyunsaturated fatty acid.

<10> The microbial oil according to any one of <1> to <9>, wherein the polyunsaturated fatty acid is at least one selected from the group consisting of eicosadienoic acid, dihomo-γ-linolenic acid, Mead acid, eicosatetraenoic acid, arachidonic acid, eicosapentaenoic acid, docosatetraenoic acid, docosapentaenoic acid and docosahexaenoic acid.

<11> The microbial oil according to any one of <8> to <10>, wherein the other saturated or unsaturated fatty acid comprises at least one selected from the group consisting of saturated fatty acids having 18 carbon atoms, monounsaturated fatty acids having 18 carbon atoms, diunsaturated fatty acids having 18 carbon atoms, triunsaturated fatty acids having 18 carbon atoms, and tetraunsaturated fatty acids having 18 carbon atoms.

<12> The microbial oil according to any one of <1> to <11>, wherein the polyunsaturated fatty acid is dihomo-γ-linolenic acid and the thermally-produced fatty acid is thermally-produced fatty acid having 20 carbon atoms.

<13> The microbial oil according to <12>, wherein the thermally-produced fatty acid comprises at least one of a first substance having a retention time with a peak appearing within a range of from 1.001 to 1.011 and a second substance having a retention time with a peak appearing within a range of from 1.013 to 1.027 in gas chromatography analysis performed under the following conditions on an ethyl ester of the thermally-produced fatty acid, wherein the retention time of ethyl dihomo-γ-linolenate is defines as 1:
Device: 6890N Network GC system (Agilent Technologies);
Column: DB-WAX, length 30 m×inside diameter 0.25 mm×film thickness 0.25 μm (Agilent Technologies);
Column temperature conditions: 2.5 minutes at 60° C.→heated at 20° C./min→180° C.→heated at 2° C./min→15 minutes at 230° C.;
Inlet temperature conditions: 210° C., splitless, split vent sampling time: 1.5 min, purge flow rate: 40 mL/min;
Injection conditions: injection volume 1 μL, sample concentration 1 mg/mL or less; Detector: FID;
Detector temperature: 280° C.; and
Carrier gas conditions: helium, linear velocity 24 cm/min.

<14> The microbial oil according to <13>, wherein the polyunsaturated fatty acid is dihomo-γ-linolenic acid, and the total content of the first substance and the second substance is from 0.001% by weight to 2.8% by weight of the total weight of fatty acids in the oil.

<15> The microbial oil according to any one of <10> to <14>, wherein the content of monounsaturated fatty acids having 18 carbon atoms is at most 7.0% by weight of the total weight of fatty acids in the oil.

<16> The microbial oil according to any one of <10> to <15>, wherein the content of monounsaturated fatty acid having 18 carbon atoms is at most 10/100 of the content of the polyunsaturated fatty acid.

<17> The microbial oil according to any one of <10> to <16>, wherein the content of diunsaturated fatty acid having 18 carbon atoms is at most 7/100 of the content of the polyunsaturated fatty acid.

<18> The microbial oil according to any one of <10> to <17>, wherein the total content of monounsaturated fatty acid having 18 carbon atoms and diunsaturated fatty acid having 18 carbon atoms is at most 15/100 of the content of the polyunsaturated fatty acid.

<19> The microbial oil according to any one of <10> to <18>, wherein the content of saturated fatty acid having 18 carbon atoms is at most 11/100 of the content of the polyunsaturated fatty acid.

<20> A production method for microbial oil comprising: providing a starting oil containing at least one polyunsaturated fatty acid having at least 20 carbon atoms in alkyl ester form and/or in free fatty acid form, obtained from microbial biomass; and performing purification on the starting oil by rectification under conditions including a column bottom temperature of from 160° C. to 230° C. and a minimum pressure in a distillation column of from 0.1 Pa to 30 Pa.

<21> A production method for microbial oil comprising: providing a starting oil containing at least one polyunsaturated fatty acid having at least 20 carbon atoms in an alkyl ester form and/or a free fatty acid form obtained from microbial biomass; performing a rectification on the starting oil using a distillation column containing structured packing under conditions including a column bottom temperature of from 160° C. to 230° C. and a minimum pressure in the distillation column of from 0.1 Pa to 30 Pa; and obtaining the microbial oil according to anyone of <1> to <19>.

<22> A production method for microbial oil comprising: providing a starting oil containing at least one polyunsaturated fatty acid having at least 20 carbon atoms in alkyl ester form and/or in free fatty acid form obtained from microbial biomass; performing rectification on the starting oil using a distillation column containing structured packing, under conditions including a column bottom temperature and a minimum pressure in the distillation column corresponding to the kind of the target polyunsaturated fatty acid, wherein microbial oil containing thermally-produced fatty acid having from 16 to 22 carbon atoms at a content of at most 3.0% by weight of the total weight of fatty acids in the oil may be obtained; and obtaining a microbial oil according to any one of <1> to <19>.

<23> The production method according to <22>, wherein the rectification is performed at a column bottom temperature of from 160° C. to 230° C. and a minimum pressure in the distillation column of from 0.1 Pa to 30 Pa.

<24> The production method according to any one of <20> to <23>, wherein the rectification comprises a plurality of cycles of rectification under mutually differing conditions for the column bottom temperature and the minimum pressure in the distillation column.

<25> The production method according to <24>, wherein the rectification comprises low-temperature rectification at a column bottom temperature of from 160° C. to 220° C. and a minimum pressure in the distillation column of from 0.1 Pa to 30 Pa; and high-temperature rectification at a column bottom temperature of from 170° C. to 230° C. and a minimum pressure in the distillation column of from 0.1 Pa to 30 Pa.

<26> The production method according to <25>, wherein the column bottom temperature in the high-temperature rectification is from 3° C. to 20° C. higher than the column bottom temperature of the low-temperature rectification.

<27> The production method according to any one of <21> to <26>, wherein the specific surface area per unit of the structured packing is from 125 $m^2/m^3$ to 1700 $m^2/m^3$.

<28> A concentrated microbial oil, the oil having: a content of polyunsaturated fatty acid having at least 20 carbon atoms in fatty acid alkyl ester form and/or in free fatty acid form of from 90% by weight to 98% by weight of the total weight of fatty acids in the oil; a content of thermally-produced fatty acid having from 16 to 22 carbon atoms of from 0.0001% by weight to 3.0% by weight of the total weight of fatty acids in the oil; a total content of saturated fatty acid having 24 carbon atoms and saturated fatty acid having 22 carbon atoms of at most 1.0% by weight of the total weight of fatty acids in the oil; and a content of monounsaturated fatty acids having 18 carbon atoms of at most 5.0% by weight of the total weight of fatty acids in the oil.

<29> A concentrated microbial oil, the oil having: a content of dihomo-γ-linolenic acid in fatty acid alkyl ester form and/or in free fatty acid form of from 90% by weight to 98% by weight of the total weight of fatty acids in the oil; a content of thermally-produced fatty acid having from 16 to 22 carbon atoms of from 0.0001% by weight to 3.0% by weight of the total weight of fatty acids in the oil; a total content of saturated fatty acid having 24 carbon atoms and saturated fatty acid having 22 carbon atoms of at most 1.0% by weight of the total weight of fatty acids in the oil; and a content of monounsaturated fatty acids having 18 carbon atoms of at most 5.0% by weight of the total weight of fatty acids in the oil.

<30> A production method for a concentrated microbial oil comprising: obtaining a microbial oil containing at least one target polyunsaturated fatty acid having at least 20 carbon atoms in fatty acid alkyl ester form and/or in free fatty acid form, using a production method according to any one of <20> to <27>; and performing concentration treatment on the obtained microbial oil using reverse phase column chromatography.

<31> Use of a microbial oil according to any one of <1> to <19> or a concentrated microbial oil according to <28> or <29> in a food product, supplement, medicament, cosmetic, or animal food.

<32> The use of a microbial oil according to any one of <1> to <19> or a concentrated microbial oil according to <28> or <29> in a production method for a food product, supplement, medicament, cosmetic, or animal food.

<33> A medicament comprising a microbial oil according to any one of <1> to <19> or a concentrated microbial oil according to <28> or <29>.

<34> An agent for preventing or treating inflammatory disease comprising a microbial oil according to any one of <1> to <19> or a concentrated microbial oil according to <28> or <29>.

<35> The agent for preventing or treating inflammatory disease according to <34>, wherein the agent is an anti-allergic agent or an anti-inflammatory agent.

<36> The agent for preventing or treating inflammatory disease according to <34> or <35>, wherein the inflammatory disease is at least one skin inflammatory disease selected from the group consisting of rashes, hives, blisters, wheal and eczema, or skin inflammatory disease caused by at least one selected from the group consisting of exposure to radiation, autoimmune diseases and uremic pruritus.

<37> The agent for preventing or treating inflammatory disease according to <34> or <35>, wherein the inflammatory disease is at least one inflammatory disease selected from the group consisting of atopic dermatitis, allergic contact dermatitis, irritant contact dermatitis, photocontact dermatitis, systemic contact dermatitis, rheumatism, psoriasis, and lupus.

<38> A method for prevention, treatment or amelioration of an inflammatory disease, the method comprising: administering the agent for preventing or treating inflammatory disease according to any one of <34> to <37> to a subject suffering from, or at risk of suffering from, the inflammatory disease.

<39> The method for prevention, treatment or amelioration of an inflammatory disease according to <37>, the administration being oral administration or local administration.

<40> A microbial oil obtained by a production method according to any one of <20> to <27>.

<41> A concentrated microbial oil obtained by a production method according to <30>.

Effect of the Invention

With the present invention, it is possible to provide a microbial oil and a production method thereof useful for efficiently obtaining a purified microbial oil containing target polyunsaturated fatty acid at a high proportion, a concentrated microbial oil containing polyunsaturated fatty acids at a high content, a production method thereof, and respective applications of the microbial oil and the concentrated microbial oil.

DESCRIPTION OF EMBODIMENTS

The production method for a microbial oil according to one aspect of the present invention comprises: providing a starting oil containing at least one polyunsaturated fatty acid having at least 20 carbon atoms in alkyl ester form and/or free fatty acid form obtained from microbial biomass; and performing a purification on the starting oil by rectification under conditions including a column bottom temperature of from 160° C. to 230° C. and a minimum pressure in the distillation column of from 0.1 Pa to 30 Pa.

The present invention is based on the knowledge that a microbial oil containing at least one target polyunsaturated fatty acid having at least 20 carbon atoms in alkyl ester form and/or free fatty acid form at a high content can be obtained by purifying a starting oil containing at least one polyunsaturated fatty acid having at least 20 carbon atoms in alkyl ester form and/or free fatty acid form obtained from microbial biomass using rectification under specific conditions.

In this specification, the at least one polyunsaturated fatty acid having at least 20 carbon atoms in alkyl ester form and/or free fatty acid form may be called a target LC-PUFA unless specified otherwise. In addition, in this specification, unless specified otherwise, the specific forms of saturated or unsaturated fatty acids in fatty acid alkyl ester form or free fatty acid form contained in the starting oil obtained from microbial biomass may be unstated. For example, unsaturated fatty acid having at least 20 carbon atoms in fatty acid alkyl ester form and unsaturated fatty acid having at least 20 carbon atoms in free fatty acid form will both be called "unsaturated fatty acids having at least 20 carbon atoms", and saturated fatty acid having 22 carbon atoms in fatty acid alkyl ester form and saturated fatty acid having 22 carbon atoms in free fatty acid form will both be called "saturated fatty acids having 22 carbon atoms".

That is, although simple distillation such as molecular distillation had been used in the past to purify a starting oil obtained from microbial biomass, with simple distillation, fatty acids are only separated by heating, and it was not possible to separate a specific target polyunsaturated fatty acid from untargeted fatty acids with good precision.

With the present invention, in a case in which a target LC-PUFA is purified from a starting oil obtained from such microbial biomass, purification is performed by rectification under specific temperature conditions and pressure conditions, so that it is possible to purify the target polyunsaturated fatty acid with good precision and with a high content.

In addition, the production method for a microbial oil according to another aspect of the present invention comprises: providing a starting oil containing at least one polyunsaturated fatty acid having at least 20 carbon atoms in alkyl ester form and/or free fatty acid form, obtained from microbial biomass; performing rectification on the starting oil using a distillation column containing structured packing under conditions including a column bottom temperature of from 160° C. to 230° C. and a minimum pressure in the distillation column of from 0.1 Pa to 30 Pa; and obtaining a specific microbial oil according to one aspect of the present invention described below.

In addition, the production method for a microbial oil according to yet another aspect of the present invention comprises: providing a starting oil containing at least one polyunsaturated fatty acid having at least 20 carbon atoms in alkyl ester form and/or free fatty acid form, obtained from microbial biomass; performing rectification on the starting oil using a distillation column containing structured packing under conditions including a column bottom temperature and a minimum pressure in the distillation column corresponding to the kind of the target polyunsaturated fatty acid, wherein a microbial oil containing thermally-produced fatty acid having from 16 to 22 carbon atoms having a content of at most 3.0% by weight of the total weight of fatty acids in the oil may be obtained; and obtaining the microbial oil according to one aspect of the present invention described below.

The microbial oil according to one aspect of the present invention is a microbial oil comprising: at least one polyunsaturated fatty acid having at least 20 carbon atoms in fatty acid alkyl ester form and/or free fatty acid form, at a content of at least 50% by weight of the total weight of fatty acids in the oil; and thermally-produced fatty acid having from 16 to 22 carbon atoms at a content of at most 3.0% by weight of the total weight of fatty acids in the oil.

In order to purify a specific fatty acid from various components contained in the starting oil by rectification with higher precision, it may be advantageous to perform rectification under more stringent conditions such as higher temperature conditions. For example, the reflux ratio (reflux flow/distillate flow) may be increased by increasing the column bottom temperature and increasing the amount of vapor so as to improve the separation of each fatty acid in rectification. In a starting oil from microbial biomass, the content of long-chain saturated fatty acids with a higher melting point than the target LC-PUFA, for example, a saturated fatty acid having 22 carbon atoms or a saturated fatty acid having 24 carbon atoms, tends to be higher than that of a well-known starting oil obtained from a fish oil, vegetable oil, or the like. It was found that long-chain saturated fatty acids in such a microbial oil have a higher molecular weight, a higher boiling point and a lower saturated vapor pressure at the same temperature than the target LC-PUFA. Accordingly, it was found that, in a case in which a starting oil derived from a microbial oil containing large amounts of these long-chain saturated fatty acids is distilled, a higher distillation temperature, that is, a higher column bottom temperature, is required than in the case of a starting oil derived from a fish oil or the like containing small amounts of these long-chain saturated fatty acids. That is, in order to distill a starting oil from microbial biomass to obtain a microbial oil in which the content of polyunsaturated fatty acids having at least 20 carbon atoms is high and the content of long-chain saturated fatty acids with an even higher melting point than these polyunsaturated fatty acids having at least 20 carbon atoms is low, there is a need for more stringent conditions, for example, higher temperature conditions than those with a well-known starting oil from a fish oil, vegetable oil, or the like. On the other hand, it was found that when distillation is performed under higher temperature conditions, fatty acid components that were not produced before distillation, so-called thermally-produced fatty acids, are generated in the microbial oil. It was found that substances produced from the target LC-PUFA as a result of being subjected to the effects of excessive heat may be considered to contain in the thermally-produced fatty acids generated in the microbial oil, and that the content of the target LC-PUFA tends to decrease along with increasing the content of thermally-produced fatty acids. It was found that thermally-produced fatty acids produced from the target LC-PUFA in the microbial oil tend not to be effectively separated from the target LC-PUFA by using reverse phase column chromatography, and that this causes decreases in the content and yield of the target LC-PUFA in a concentrated microbial oil. It was ascertained from these findings that even in a case in which purification is performed on a microbial oil with a reduced content of the target LC-PUFA using reverse phase column chromatography, this purification is not efficient.

Focusing attention on such thermally-produced fatty acids, the present invention is based on the knowledge that, due to the relationship between the precision of the purification for the target LC-PUFA and increases in the content of thermally-produced fatty acids having from 16 to 22 carbon atoms, it is unexpectedly possible to perform purification simply and efficiently to obtain a target LC-PUFA with a high content by performing rectification using a distillation column containing structured packing or by performing rectification so as to contain a certain amount of thermally-produced fatty acids having from 16 to 22 carbon atoms. In addition, focusing attention on such thermally-produced fatty acids having from 16 to 22 carbon atoms, the present invention is based on the knowledge that, due to the relationship between the precision of the purification for the target LC-PUFA and increases in the content of thermally-produced fatty acids having from 16 to 22 carbon atoms, a microbial oil containing a certain amount of thermally-produced fatty acids having from 16 to 22 carbon atoms is unexpectedly more advantageous for more efficiently obtaining a microbial oil containing the target LC-PUFA at a high content. In this specification, unless specified otherwise, thermally-produced fatty acids having from 16 to 22 carbon atoms may be simply called "thermally-produced fatty acid".

A concentrated microbial oil containing a target LC-PUFA at a high content may be obtained from a microbial oil according to the present invention, and from a microbial oil obtained by the production method according to the present invention, by further using a specific concentrating means such as reverse phase column chromatography.

That is, the concentrated microbial oil according to another aspect of the present invention is a concentrated microbial oil, in which the content of polyunsaturated fatty acids having at least 20 carbon atoms in fatty acid alkyl ester form and/or free fatty acid form is from 90% by weight to 98% by weight of the total weight of fatty acids in the oil; the content of thermally-produced fatty acids having from 16 to 22 carbon atoms is from 0.0001% by weight to 3.0% by weight of the total weight of fatty acids in the oil; the total content of saturated fatty acids having 24 carbon atoms and saturated fatty acids having 22 carbon atoms is at most 1.0% by weight of the total weight of fatty acids in the oil; and the content of monounsaturated fatty acids having 18 carbon atoms is at most 5.0% by weight of the total weight of fatty acids in the oil.

The production method for a concentrated microbial oil according to another aspect of the present invention comprises: obtaining a microbial oil containing at least one target polyunsaturated fatty acid having at least 20 carbon atoms in fatty acid alkyl ester form and/or free fatty acid form, using any one of the production methods for microbial oil according to other aspects of the present invention; and performing concentration treatment on the obtained microbial oil using reverse phase column chromatography.

The concentrated microbial oil or the microbial oil according to aspects of the present invention comprises or may comprise a target LC-PUFA at a high content, and is therefore useful in fields such as food products, supplements, medicaments, cosmetics and animal foods, and, for example, for an agent for preventing or treating inflammatory disease or a method for prevention, treatment or amelioration of an inflammatory disease. In addition, with the production method for a concentrated microbial oil according to an aspect of the present invention, the production method of the present invention capable of efficiently obtaining a microbial oil containing the target LC-PUFA at a high content is used, so that a concentrated microbial oil can be provided efficiently.

In the present specification, the scope of the term "process" includes not only a discrete process, but also a process that cannot be clearly distinguished from another process as long as the expected effect of the process of interest is achieved.

In the present specification, any numerical range expressed using "to" refers to a range including the numerical values before and after "to" as the minimum and maximum values, respectively.

In a case in which the amount of a component type that may be included in the mixture is indicated herein, when there are plural substances corresponding to the component type in the mixture, the indicated amount means the total amount of the plural substances present in the mixture, unless specifically stated otherwise.

In a case in which the content of a component type that may be included in the mixture is indicated herein, when there are plural substances corresponding to the component type in the mixture, the indicated content means the total content of the plural substances present in the mixture, unless specifically stated otherwise.

In the present invention, "microbial oil" is a mixture of organic substances which is obtained using microbial biomass as a source and which is insoluble in water at normal temperature and normal pressure. A microbial oil contains oily components such as saturated or unsaturated fatty acids, phospholipids, sterols, glycerols, ceramides, sphingolipids, terpenoids, flavonoids and tocopherols, and saturated or unsaturated fatty acids may also be present as constituent fatty acids in such other oily components.

In the present invention, "fatty acid" refers to fatty acid contained as free saturated or unsaturated fatty acid, saturated or unsaturated fatty acid alkyl ester, triacylglycerol, diacylglycerol, monoacylglycerol, phospholipid, steryl ester or the like, and may be interchangeably described as constituent fatty acid.

In this specification, unless specified otherwise, the form of compound containing a fatty acid may be unstated. Examples of forms of compound containing fatty acid include the free fatty acid form, fatty acid alkyl ester form, glyceryl ester form, phospholipid form, steryl ester form and the like. Compound containing the same fatty acid may be contained in a single form or may be contained as a mixture of two or more forms in the microbial oil.

In addition, when expressing fatty acids, a numerical expression may be used whereby the number of carbon atoms, the number of double bonds, and the locations of double bonds are expressed in a simplified manner using numbers and the alphabet respectively. For example, a saturated fatty acid having 20 carbon atoms may be notated as "C20:0". A monounsaturated fatty acid having 18 carbon atoms may be notated as "C18:1" or the like. Dihomo-γ-linolenic acid may be notated as "C20:3, n-6" or the like. Arachidonic acid may be expressed as "C20:4, n-6" or the like. This method is known to those of ordinary skill in the art, and a person of ordinary skill in the art can easily specify fatty acids in accordance with this method.

The total content of fatty acids in the microbial oil may be, for example, at least 80% by weight, at least 90% by weight, at least 95% by weight, or at least 98% by weight of the total weight of the microbial oil. Examples of other components which may be present in the microbial oil, and which are compounds not containing fatty acid or partial structures other than fatty acids of compounds containing fatty acids, include glycerins, sterols, hydrocarbons, terpenoids, flavonoids, tocopherols, and glycerin skeleton partial structures of glyceryl esters, phosphate skeleton partial structures of phosphoric acids, sphingosine skeleton partial structures and the like.

In this specification, a mixture of compounds in a state simply extracted from microbial biomass may be called a crude oil of a microbial oil.

Unless a specific type of fatty acid is specified, fatty acid alkyl ester or free fatty acid in the present invention indicates a mixture of fatty acid alkyl esters or a mixture of free fatty acids obtained by performing a process such as hydrolysis or alkyl esterification on a crude oil obtained from microbial biomass.

The content of fatty acids with respect to the total weight of fatty acids in the oil in the present invention is determined based on the fatty acid composition. The fatty acid composition may be determined by a normal method. Specifically, the oil to be measured is esterified using a lower alcohol and a catalyst to obtain fatty acid lower alkyl ester. Next, the obtained fatty acid lower alkyl ester is analyzed using a gas chromatograph with a flame ionization detector (FID). The peaks corresponding to each of the fatty acids are identified in the obtained gas chromatography chart, and the peak areas of each of the fatty acids are determined using the Agilent ChemStation integration algorithm (revision C.01.03[37], Agilent Technologies). The fatty acid compositions are determined as the percentage of each peak area to the sum of the peak areas of the peaks of the fatty acids. The area % obtained by the measurement method described above is determined to be the same as the % by weight of each fatty acid in the sample. Refer to "The JOCS Standard Methods for the Analysis of Fats, Oils and Related Materials", 2013 Edition, 2.4.2.1-2013 Fatty Acid Composition (FID gas chromatography) and 2.4.2.2-2013 Fatty Acid Composition (FID temperature programmed gas chromatography) established by the Japan Oil Chemists' Society (JOCS).

In a case in which the microbial oil contains fatty acids other than fatty acids in the fatty acid alkyl ester form and the free fatty acid form, the fatty acid composition to be measured is measured after the fatty acids other than fatty acids in the fatty acid alkyl ester form and fatty acids in the free fatty acid form are separated from the microbial oil. As an example of a method for separating fatty acids other than fatty acids in the fatty acid alkyl ester form and the free fatty acid form from the microbial oil, it is possible to refer to methods such as the silicic acid column chromatography disclosed in The Journal of Biological Chemistry, 1958, 233:311-320 or the thin-layer chromatography disclosed in The Lipid Handbook with CD-ROM, Third Edition, CRC Press Taylor & Francis Group (2007).

Each aspect of the present invention will be described hereinafter.

(1) Microbial Oil

The microbial oil according to one aspect of the present invention comprises at least one polyunsaturated fatty acid having at least 20 carbon atoms in fatty acid alkyl ester form and/or in free fatty acid form, at a content of at least 50% by weight of the total weight of fatty acids in the oil; and thermally-produced fatty acid having from 16 to 22 carbon atoms at a content of at most 3.0% by weight of the total weight of fatty acids in the oil.

As described above, the microbial oil may be obtained using microbial biomass as a source. The microbe may be a lipid-producing microbe, examples of which are algae and fungi.

Examples of algae include the genus *Labyrinthula* (*Labyrinthula mycota*) and the like.

Examples of fungi include at least one selected from the group consisting of the genus *Mortierella*, the genus *Conidiobolus*, the genus *Pythium*, the genus *Phytophthora*, the genus *Penicillium*, the genus *Cladosporium*, the genus *Mucor*, the genus *Fusarium*, the genus *Aspergillus*, the genus *Rhodotorula*, the genus *Entomophthora*, the genus *Echinosporangium* and the genus *Saprolegnia*. Of these, microbes belonging to the genus *Mortierella* are even more preferable. Examples of microbes belonging to the genus *Mortierella* include microbes belonging to the *Mortierella* subgenus such as *Mortierella elongata, Mortierella exigua, Mortierella hygrophila* and *Mortierella alpina*.

The polyunsaturated fatty acid having at least 20 carbon atoms in the present invention includes di- or higher-unsaturated fatty acid and preferably tri- or higher-unsaturated fatty acid. The number of carbon atoms of the polyunsaturated fatty acid refers to the number of carbon atoms of the constituent fatty acids. Examples of polyunsaturated fatty acids having at least 20 carbon atoms include polyunsaturated fatty acids having at least 20 and at most 22 carbon atoms, specific examples of which include eicosadienoic acid (C20:2, n-9), dihomo-γ-linolenic acid (C20:3, n-6), Mead acid (C20:3, n-9), eicosatetraenoic acid (C20:4, n-3), arachidonic acid (C20:4, n-6), eicosapentaenoic acid (C20:5, n-3), docosatetraenoic acid (C22:4, n-6), docosapentaenoic acid (C22:5, n-3), docosapentaenoic acid (C22:5, n-6), docosahexaenoic acid (C22:6, n-3) and the like. The microbial oil may comprise at least one of these polyunsaturated fatty acids and may also contain two or more in combination. The microbial oil may also be an oil containing one type selected from these polyunsaturated fatty acids and not containing other polyunsaturated fatty acids. The microbial oil may be an oil that does not contain one or two or more specific types, as long as the microbial oil contains at least one type selected from the polyunsaturated fatty acids having at least 20 and at most 22 carbon atoms described above as the target LC-PUFA. For example, the microbial oil may not contain at least one selected from the group consisting of eicosadienoic acid (C20:2, n-9), dihomo-γ-linolenic acid (C20:3, n-6), Mead acid (C20:3, n-9), eicosatetraenoic acid (C20:4, n-3), arachidonic acid (C20:4, n-6), eicosapentaenoic acid (C20:5, n-3), docosatetraenoic acid (C22:4, n-6), docosapentaenoic acid (C22:5, n-3), docosapentaenoic acid (C22:5, n-6), and docosahexaenoic acid (C22:6, n-3). The phrase, "not containing polyunsaturated fatty acids" means that the content of the polyunsaturated fatty acid to be subject is 0 or less than 5% by weight of the total weight of fatty acids in the oil.

Preferable examples of alkyl groups of polyunsaturated fatty acids in the fatty acid alkyl ester form include alkyl groups having from 1 to 3 carbon atoms, examples of which include methyl groups, ethyl groups, propyl groups, and the like. Polyunsaturated fatty acids in the alkyl ester form are particularly preferably polyunsaturated fatty acids in the ethyl ester form or the methyl ester form.

The content of the target LC-PUFA in the microbial oil, that is, polyunsaturated fatty acids having at least 20 carbon atoms in the fatty acid alkyl ester form and/or free fatty acid form, is at least 50% h by weight of the total weight of fatty acids in the oil. When the content of the target LC-PUFA is less than 50% by weight, it is not possible to efficiently obtain a purified microbial oil containing the target LC-PUFA with a high content. As described above, the content of the target LC-PUFA in the microbial oil is a value obtained by analyzing the fatty acid composition of the microbial oil.

From the perspective of more efficiently achieving the purification of the target LC-PUFA, the content of the target LC-PUFA in the microbial oil is preferably at least 60% by weight, more preferably at least 70% by weight, even more preferably at least 80% by weight, even more preferably at least 85% by weight, particularly preferably at least 90% by weight, even more particularly preferably at least 95% by weight, and most preferably 98% by weight of the total weight of fatty acids in the oil. The content of the target LC-PUFA in the microbial oil may be from 50% by weight to 98% by weight, from 60% by weight to 98% by weight, from 70% by weight to 98% by weight, from 80% by weight to 98% by weight, from 85% by weight to 98% by weight, from 90% by weight to 98% by weight, or from 95% by weight to 98% by weight of the total weight of fatty acids in the oil.

The microbial oil of the present invention comprises the thermally-produced fatty acid having from 16 to 22 carbon atoms at a content of at most 3.0% by weight of the total weight of fatty acids in the oil.

As described above, the thermally-produced fatty acid is fatty acid having from 16 to 22 carbon atoms that is generated based on the presence of the target LC-PUFA due to heat associated with high-temperature treatment such as distillation. That is, the thermally-produced fatty acid is considered to be fatty acid that is produced as a result of the target LC-PUFA causing degradation, isomerization, or the like due to heat associated with high-temperature treatment such as distillation, but the present invention is not limited to this theory. The form of thermally-produced fatty acid is not particularly limited and is not limited to the fatty acid alkyl ester form or the free fatty acid form.

The number and types of the thermally-produced fatty acids contained in the microbial oil differ depending on the conditions of rectification, the type of target LC-PUFA contained in the microbial oil, and the like.

It is conceived that examples of the thermally-produced fatty acids are trans isomers of the target LC-PUFA (see the Journal of the American Oil Chemists' Society, Vol. 66, No. 12, pp. 1822-1830 (1989)). That is, whereas the carbon double bond portions contained in the target LC-PUFA are ordinarily cis form, the thermally-produced fatty acids may be substances in which some or all of the carbon double bond portions are converted to the trans form, substances having conjugated double bonds as a result of the modification of the positions of double bonds, or the like.

The following are examples of the thermally-produced fatty acids. The microbial oil may contain any one or a combination of two or more of the following compounds: 8Z,11E-eicosadienoic acid, 8E,11Z-eicosadienoic acid, 8E,11E-eicosadienoic acid, 8Z,11Z,14E-eicosatrienoic acid, 8Z,11E,14Z-eicosatrienoic acid, 8E,11Z,14Z-eicosatrienoic acid, 8Z,11E,14E-eicosatrienoic acid, 8E,11Z,14E-eicosatrienoic acid, 8E,11E,14Z-eicosatrienoic acid, 8E,11E,14E-eicosatrienoic acid, 5Z,8Z,11E-eicosatrienoic acid, 5Z,8E,11Z-eicosatrienoic acid, 5E,8Z,11Z-eicosatrienoic acid, 5Z,8E,11E-eicosatrienoic acid, 5E,8Z,11E-eicosatrienoic acid, 5E,8E,11Z-eicosatrienoic acid, 5E,8E,11E-eicosatrienoic acid, 8Z,11Z,14Z,17E-eicosatetraenoic acid, 8Z,11Z,14E,17Z-eicosatetraenoic acid, 8Z,11E,14Z,17Z-eicosatetraenoic acid, 8E,11Z,14Z,17Z-eicosatetraenoic acid, 8E,11Z,14Z,17E-eicosatetraenoic acid, 8Z,11Z,14E,17E-eicosatetraenoic acid, 8Z,11E,14Z,17E-eicosatetraenoic acid, 8Z,11E,14E,17Z-eicosatetraenoic acid, 8E,11Z,14E,17Z-eicosatetraenoic acid, 8E,11E,14Z,17Z-eicosatetraenoic acid, 8E,11E,14Z,17E-eicosatetraenoic acid, 8E,11Z,14E,17E-eicosatetraenoic acid, 8E,11E,14E,17Z-eicosatetraenoic acid, 8Z,11E,14E,17E-eicosatetraenoic acid, 8E,11E,14E,17E-eicosatetraenoic acid, 5Z,8Z,11Z,14-eicosatetraenoic acid, 5Z,8Z,11E,14Z-eicosatetraenoic acid, 5Z,8E,11Z,14Z-eicosatetraenoic acid, 5E,8Z,11Z,14Z-eicosatetraenoic acid, 5Z,8Z,11E,14E-eicosatetraenoic acid, 5Z,8E,11Z,14E-eicosatetraenoic acid, 5E,8Z,11Z,14E-eicosatetraenoic acid, 5Z,8E,11E,14Z-eicosatetraenoic acid, 5E,8Z,11E,14Z-eicosatetraenoic acid, 5E,8E,11Z,14Z-eicosatetraenoic acid, 5E,8E,11Z,14Z-eicosatetraenoic acid, 5E,8E,11E,14Z-eicosatetraenoic acid, 5E,8Z,11E,14E-eicosatetraenoic acid, 5Z,8E,11E,14E-eicosatetraenoic acid, 5E,8E,11E,14Z-eicosatetraenoic acid, 5Z,8Z,11Z,14E,17E-eicosapentaenoic acid, 5Z,8Z,11Z,14E,17Z-eicosapentaenoic acid, 5Z,8Z,11E,14Z,17Z-eicosapentaenoic acid, 5Z,8E,11Z,14Z,17Z-eicosapentaenoic acid, 5E,8Z,11Z,14Z,17Z-eicosapentaenoic acid, 5E,8Z,11Z,14Z,17E-eicosapentaenoic acid, 5Z,8E,11Z,14Z,17E-eicosapentaenoic acid, 5Z,8Z,8E,14Z,17E-eicosapentaenoic acid, 5Z,8Z,11Z,14E,17E-eicosapentaenoic acid, 5E,8Z,11Z,14E,17Z-eicosapentaenoic acid, 5Z,8E,11Z,14E,17Z-eicosapentaenoic acid, 5Z,8Z,11E,14E,17Z-eicosapentaenoic acid, 5E,8Z,11E,14Z,17Z-eicosapentaenoic acid, 5Z,8E,11E,14Z,17Z-eicosapentaenoic acid, 5E,8E,11Z,14Z,17Z-eicosapentaenoic acid, 5Z,8E,11E,14Z,17E-eicosapentaenoic acid, 5E,8Z,11E,14Z,17E-eicosapentaenoic acid, 5E,8Z,11Z,14E,17E-eicosapentaenoic acid, 5E,8E,11Z,14E,17Z-eicosapentaenoic acid, 5E,8E,11Z,14Z,17E-eicosapentaenoic acid, 5E,8E,11E,14Z,17Z-eicosapentaenoic acid, 5Z,8E,11E,14Z-eicosapentaenoic acid, 5E,8Z,11E,14Z,17E-eicosapentaenoic acid, 5E,8E,11Z,14Z,17E-eicosapentaenoic acid, 5E,8E,11E,14Z,17E-eicosapentaenoic acid, 5Z,8E,11E,14E,17Z-eicosapentaenoic acid, 5E,8Z,11E,14E,17Z-eicosapentaenoic acid, 5Z,8Z,11E,14E,17E-eicosapentaenoic acid, 5E,8E,11E,14Z,17E-eicosapentaenoic acid, 5E,8E,11E,14E,17Z-eicosapentaenoic acid, 5E,8Z,11E,14E,17E-eicosapentaenoic acid, 5Z,8E,11E,14E,17E-eicosapentaenoic acid, 5E,8E,11E,14E,17E-eicosapentaenoic acid, 7Z,10Z,13Z,16Z,19E-docosapentaenoic acid, 7Z,10Z,13Z,16E,19Z-docosapentaenoic acid, 7Z,10Z,13E,16Z,19Z-docosapentaenoic acid, 7Z,10E,13Z,16Z,19Z-docosapentaenoic acid, 7E,10Z,13Z,16Z,19Z-docosapentaenoic acid, 7E,10Z,13Z,16Z,19E-docosapentaenoic acid, 7Z,10E,13Z,16Z,19E-docosapentaenoic acid, 7Z,10Z,13E,16Z,19E-docosapentaenoic acid, 7Z,10Z,13Z,16E,19E-docosapentaenoic acid, 7E,10Z,13Z,16E,19Z-docosapentaenoic acid, 7Z,10E,13Z,16E,19Z-docosapentaenoic acid, 7Z,10Z,13E,16E,19Z-docosapentaenoic acid, 7E,10Z,13E,16Z,19Z-docosapentaenoic acid, 7Z,10E,13E,16Z,19Z-docosapentaenoic acid, 7E,10E,13Z,16Z,19Z-docosapentaenoic acid, 7E,10E,13Z,16Z,19E-docosapentaenoic acid, 7Z,10E,13E,16Z,19E-docosapentaenoic acid, 7E,10Z,13E,16Z,19E-docosapentaenoic acid, 7Z,10E,13Z,16E,19E-docosapentaenoic acid, 7E,10Z,13Z,16E,19E-docosapentaenoic acid, 7Z,10Z,13E,16E,19E-docosapentaenoic acid, 7E,10E,13E,16Z,19E-docosapentaenoic acid, 7E,10E,13Z,16E,19E-docosapentaenoic acid, 7E,10Z,13E,16E,19E-docosapentaenoic acid, 7Z,10E,13E,16E,19E-docosapentaenoic acid, 7E,10E,13E,16E,19Z-docosapentaenoic acid, 7E,10E,13E,16E,19E-docosapentaenoic acid, 4Z,7Z,10Z,13Z,16Z,19E-docosahexaenoic acid, 4Z,7Z,10Z,13Z,16E,19Z-docosahexaenoic acid, 4Z,7Z,10Z,13E,16Z,19Z-docosahexaenoic acid, 4Z,7Z,10E,13Z,16Z,19Z-docosahexaenoic acid, 4Z,7E,10Z,13Z,16Z,19Z-docosahexaenoic acid, 4E,7Z,10Z,13Z,16Z,19Z-docosahexaenoic acid, 4E,7Z,10Z,13Z,16Z,19E-docosahexaenoic acid, 4Z,7E,10Z,13Z,16Z,19E-docosahexaenoic acid, 4Z,7Z,10E,13Z,16Z,19E-docosahexaenoic acid, 4Z,7Z,10Z,13E,16Z,19E-docosahexaenoic acid, 4Z,7Z,10Z,13Z,16E,19E-docosahexaenoic acid, 4E,7Z,10Z,13Z,16E,19Z-docosahexaenoic acid, 4Z,7E,10Z,13Z,16E,19Z-docosahexaenoic acid, 4Z,7Z,10E,13Z,16E,19Z-docosahexaenoic acid, 4Z,7Z,10Z,13E,16E,19Z-docosahexaenoic acid, 4E,7Z,10Z,13E,16Z,19Z-docosahexaenoic acid, 4Z,7E,10Z,13E,16Z,19Z- docosahexaenoic acid, 4Z,7Z,10E,13E,16Z,19Z-docosahexaenoic acid, 4E,7Z,10E,13E,16Z,19Z-docosahexaenoic acid, 4Z,7E,10E,13E,16Z,19Z-docosahexaenoic acid, 4E,7E,10Z,13Z,16Z,19Z-docosahexaenoic acid, 4E,7E,10E,13Z,16Z,19Z-docosahexaenoic acid, 4E,7E,10Z,13E,16Z,19Z-docosahexaenoic acid, 4E,7E,10Z,13Z,16E,19Z-docosahexaenoic acid, 4E,7E,10Z,13Z,16Z,19E-docosahexaenoic acid, 4E,7Z,10E,13E,16Z,19Z-docosahexaenoic acid, 4E,7Z,10E,13Z,16E,19Z-docosahexaenoic acid, 4E,7Z,10E,13Z,16Z,19E-docosahexaenoic acid, 4E,7Z,10Z,13E,16E,19Z-docosahexaenoic acid, 4E,7Z,10Z,13E,16Z,19E-docosahexaenoic acid, 4E,7Z,10Z,13Z,16E,19E-docosahexaenoic acid, 4Z,7E,10E,13E,16Z,19Z-docosahexaenoic acid, 4Z,7E,10E,13Z,16E,19Z-docosahexaenoic acid, 4Z,7E,10E,13Z,16Z,19E-docosahexaenoic acid, 4Z,7E,10Z,13E,16E,19Z-docosahexaenoic acid, 4Z,7E,10Z,13E,16Z,19E-docosahexaenoic acid, 4Z,7E,10Z,13Z,16E,19E-docosahexaenoic acid, 4Z,7Z,10E,13E,16E,19Z-docosahexaenoic acid, 4Z,7Z,10E,13E,16Z,19E-docosahexaenoic acid, 4Z,7Z,10E,13Z,16E,19E-docosahexaenoic acid, 4Z,7Z,10Z,13E,16E,19E-docosahexaenoic acid, 4Z,7E,10E,13E,16E,19Z-docosahexaenoic acid, 4Z,7E,10E,13E,16Z,19E-docosahexaenoic acid, 4Z,7E,10E,13Z,16E,19E-docosahexaenoic acid, 4Z,7E,10Z,13E,16E,19E-docosahexaenoic acid, 4E,7Z,10Z,13E,16E,19E-docosahexaenoic acid, 4E,7Z,10E,13Z,16E,19E-docosahexaenoic acid, 4E,7Z,10E,13E,16Z,19E-docosahexaenoic acid, 4E,7Z,10E,13E,16E,19Z-docosahexaenoic acid, 4E,7E,10Z,13Z,16E,19E-docosahexaenoic acid, 4E,7E,10Z,13E,16Z,19E-docosahexaenoic acid, 4E,7E,10Z,13E,16E,19Z-docosahexaenoic acid, 4E,7E,10E,13Z,16Z,19E-docosahexaenoic acid, 4E,7E,10E,13Z,16E,19Z-docosahexaenoic acid, 4E,7E,10E,13E,16Z,19Z-docosahexaenoic acid, 4Z,7E,10E,13E,16E,19E-docosahexaenoic acid, 4E,7Z,10E,13E,16E,19E-docosahexaenoic acid, 4E,7E,10Z,13E,16E,19E-docosahexaenoic acid, 4E,7E,10E,13Z,16E,19E-docosahexaenoic acid, 4E,7E,10E,13E,16Z,19E-docosahexaenoic acid, 4E,7E,10E,13E,16E,19Z-docosahexaenoic acid, 4E,7E,10E,13E,16E,19E-docosahexaenoic acid, 7Z,10Z,13Z,16E-docosatetraenoic acid, 7Z,10Z,13E,16Z-docosatetraenoic acid, 7Z,10E,13Z,16Z-docosatetraenoic acid, 7E,10Z,13Z,16Z-docosatetraenoic acid, 7E,10Z,13Z,16E-docosatetraenoic acid, 7Z,10E,13Z,16E-docosatetraenoic acid, 7Z,10Z,13E,16E-docosatetraenoic acid, 7E,10Z,13E,16Z-docosatetraenoic acid, 7Z,10E,13E,16Z-docosatetraenoic acid, 7E,10E,13Z,16Z-docosatetraenoic acid, 7E,10Z,13E,16E-docosatetraenoic acid, 7E,10E,13Z,16E-docosatetraenoic acid, 7E,10E,13E,16Z-docosatetraenoic acid, 7E,10E,13E,16E-docosatetraenoic acid, 4Z,7Z,10Z,13Z,16E-docosapentaenoic acid, 4Z,7Z,10Z,13E,16Z-docosapentaenoic acid, 4Z,7Z,10E,13Z,16Z-docosapentaenoic acid, 4Z,7E,10Z,13Z,16Z-docosapentaenoic acid, 4E,7Z,10Z,13Z,16Z-docosapentaenoic acid, 4E,7Z,10Z,13Z,16E-docosapentaenoic acid, 4Z,7E,10Z,13Z,16E-docosapentaenoic acid, 4Z,7Z,10E,13Z,16E-docosapentaenoic acid, 4Z,7Z,10Z,13E,16E-docosapentaenoic acid, 4E,7Z,10Z,13E,16Z-docosapentaenoic acid, 4Z,7E,10Z,13E,16Z-docosapentaenoic acid, 4Z,7Z,10E,13E,16Z-docosapentaenoic acid, 4E,7Z,10E,13Z,16Z-docosapentaenoic acid, 4Z,7E,10E,13Z,16Z-docosapentaenoic acid, 4E,7E,10Z,13Z,16Z-docosapentaenoic acid, 4E,7E,10Z,13Z,16E-docosapentaenoic acid, 4E,7E,10E,13Z,16Z-docosapentaenoic acid, 4E,7E,10Z,13E,16Z-docosapentaenoic acid, 4E,7E,10Z,13Z,16E-docosapentaenoic acid, 4E,7Z,10E,13Z,16E-docosapentaenoic acid, 4E,7Z,10E,13E,16Z-docosapentaenoic acid, 4E,7Z,10Z,13E,16E-docosapentaenoic acid, 4Z,7E,10E,13Z,16E-docosapentaenoic acid, 4Z,7E,10Z,13E,16E-docosapentaenoic acid, 4Z,7E,10E,13E,16Z-docosapentaenoic acid, 4Z,7E,10Z,13E,16E-docosapentaenoic acid, 4Z,7E,10E,13E,16Z-docosapentaenoic acid, 4Z,7E,10E,13E,16E-docosapentaenoic acid, 4E,7Z,10E,13E,16E-docosapentaenoic acid, 4E,7E,10Z,13E,16E-docosapentaenoic acid, 4E,7E,10E,13Z,16E-docosapentaenoic acid, 4E,7E,10E,13E,16Z-docosapentaenoic acid, 4E,7E,10E,13E,16E-docosapentaenoic acid.

In a case in which the content of the thermally-produced fatty acid in the microbial oil exceeds 3.0% by weight, it is not possible to efficiently obtain a microbial oil containing the target LC-PUFA at a high content. Since the microbial oil is obtained via a heating process including distillation, the thermally-produced fatty acid may be contained in the microbial oil at a content of from 0.0001% by weight to 3.0% by weight, a content of from 0.001% by weight to 3.0% by weight, or a content of from 0.01% by weight to 3.0% by weight.

From the perspective of efficiently obtaining a concentrated microbial oil containing the target LC-PUFA at a high content using reverse phase column chromatography, the content of the thermally-produced fatty acid in the microbial oil may be from 0.001% by weight to 2.8% by weight, from 0.01% by weight to 2.8% by weight, from 0.1% by weight to 2.8% by weight, from 0.1% by weight to 2.5% by weight, from 0.1% by weight to 2.0% by weight, from 0.1% by weight to 1.5% by weight, from 0.1% by weight to 1.0% by weight, or from 0.1% by weight to 0.7% by weight of the total weight of fatty acids in the oil.

The thermally-produced fatty acids are fatty acids having from 16 to 20 carbon atoms that are detectable after treatment by rectification and are not detected prior to this treatment. Therefore, the fatty acid compositions before and after distillation treatment can be compared using, for example, various types of chromatographic analysis and the thermally-produced fatty acids may be specified as fatty acids having peaks that appear after the distillation treatment. Of these types of chromatography, gas chromatography in particular may be used from the perspective of its high analytical capacity or detection sensitivity or relatively simple operation. In order to specify the thermally-produced fatty acids with even higher precision, the thermally-produced fatty acid may be analyzed and specified after removing components originating from the microbial biomass which overlap with the thermally-produced fatty acids, for example, by silver-ion solid phase extraction using silver-ion chromatography.

For example, in a case in which the target LC-PUFA is dihomo-γ-linolenic acid (DGLA), the thermally-produced fatty acid may be thermally-produced fatty acid having 20 carbon atoms. Examples of the thermally-produced fatty acids having 20 carbon atoms include are one or two or more the thermally-produced fatty acids having 20 carbon atoms (called Compound A hereafter) having a retention time with a peak appearing within the range of from 1.001 to 1.011 and one or two or more thermally-produced fatty acids (called Compound B hereafter) having a retention time with a peak appearing within the range of from 1.013 to 1.027, where the retention time of ethyl dihomo-γ-linolenate is defined as 1 in gas chromatography analysis. Compound A and Compound B may be one or groups of two or more compounds, or Compound A and Compound B may each be single compounds. The thermally-produced fatty acids may be Compound A, Compound B, or both Compounds A and B. The conditions of gas chromatography in a case in which Compound A and Compound B are specified as thermally-produced fatty acids are as follows:

[Gas Chromatography Analysis Conditions]

GC device: 6890N Network GC system (Agilent Technologies)

Column: DB-WAX (Agilent Technologies)
        30 m×0.25 mm ID, 0.25 µm film thickness Column temperature conditions: 2.5 minutes at 60° C.→heated at 20° C./min→180° C.→heated at 2° C./min→15 minutes at 230° C.

Inlet temperature conditions: 210° C., splitless, split vent sampling time 1.5 min, purge flow rate 40 mL/min Injection conditions: injection volume 1 µL, sample concentration at most 1 mg/mL Carrier gas conditions: helium, linear velocity 24 cm/min Detector: FID Detector temperature: 280° C.

From the perspective of the purification efficiency of DGLA the content of Compound A and Compound B, which are the thermally-produced fatty acids in a case in which the target LC-PUFA is DGLA, in the microbial oil may be from 0.001% by weight to 2.8% by weight, from 0.1% by weight to 2.8% by weight, from 0.1% by weight to 2.5% by weight, from 0.1% by weight to 2.0% by weight, from 0.1% by weight to 1.5% by weight, from 0.1% by weight to 1.0% by weight, or from 0.1% by weight to 0.7% by weight of the total weight of fatty acids in the oil.

The microbial oil of the present invention is preferably a composition in which the content of at least one specific fatty acid to be separated from the target LC-PUFA by rectification is low. In this specification, unless specified otherwise, a fatty acid to be separated from the target LC-PUFA in the purification process will be called a separation target fatty acid. The separation target fatty acid is not particularly limited as long as it is a fatty acid other than the target LC-PUFA. The form of the separation target fatty acid is also not particularly limited, and the form of the separation target fatty acid may be a fatty acid alkyl ester form, free fatty acid form, or the like.

Examples of the separation target fatty acids include saturated fatty acids having 22 carbon atoms and saturated fatty acids having 24 carbon atoms. The content of saturated fatty acids having 22 carbon atoms and saturated fatty acids having 24 carbon atoms in a crude oil obtained from microbial biomass typically tends to be higher than that of fish oil or animal or plant oils. Saturated fatty acids having 22 carbon atoms and saturated fatty acids having 24 carbon atoms are long-chain fatty acids with a higher melting point than that of the target LC-PUFA. Reduction of the contents of saturated fatty acids having 22 carbon atoms and saturated fatty acids having 24 carbon atoms may suppress the clogging of piping in column chromatography treatment, which makes it possible to perform reverse phase column chromatography. The retention times of saturated fatty acids having 22 carbon atoms and saturated fatty acids having 24 carbon atoms in reverse phase column chromatography may be longer than that of the target LC-PUFA, and this may be a factor contributing to a lengthening of the time required for chromatography, so reducing the contents of these saturated fatty acids is also preferable from the perspective of the purification efficiency per unit time.

In a case in which saturated fatty acids having 22 carbon atoms and saturated fatty acids having 24 carbon atoms are respectively present, the total content of saturated fatty acids having 22 carbon atoms and saturated fatty acids having 24 carbon atoms refers to the total content of both types of fatty acids, and in a case in which only one type is present, the total content of saturated fatty acids having 22 carbon atoms and saturated fatty acids having 24 carbon atoms refers to the content of only the type that is present.

The total content of saturated fatty acid having 22 carbon atoms and saturated fatty acid having 24 carbon atoms in the microbial oil is preferably at most 6.0% by weight, even more preferably at most 1.8% by weight, and even more preferably at most 0.1% by weight of the total weight of fatty acids in the oil, from the perspective of the suppression of the clogging of piping in column chromatography and the perspective of the purification efficiency of the target LC-PUFA. The total content of saturated fatty acid having 22 carbon atoms and saturated fatty acid having 24 carbon atoms in the microbial oil is preferably at most 10/100, more preferably at most 3/100, and even more preferably at most 0.1/100 of the content of the target LC-PUFA from the perspective of the suppression of the clogging of piping in column chromatography and the perspective of the purification efficiency of the target LC-PUFA. The total content of saturated fatty acid having 22 carbon atoms and saturated fatty acid having 24 carbon atoms in the microbial oil is preferably at most 6.0% by weight, more preferably at most 1.0% by weight, and even more preferably at most 0.1% by weight with respect to the total weight of the microbial oil from the perspective of the suppression of the clogging of piping in column chromatography and the perspective of the purification efficiency of the target LC-PUFA.

In addition, the content of saturated fatty acid having 24 carbon atoms in the microbial oil is more preferably at most 3.0% by weight, even more preferably at most 1.0% by weight, and even more preferably at most 0.1% by weight of the total weight of fatty acids in the oil from the perspective of the suppression of the clogging of piping in column chromatography and the perspective of the purification efficiency of the target LC-PUFA. The content of saturated fatty acid having 24 carbon atoms in the microbial oil is preferably at most 4/100, more preferably at most 1.4/100, and even more preferably at most 0.1/100 of the content of the target LC-PUFA from the perspective of the suppression of the clogging of piping in column chromatography and the perspective of the purification efficiency of the target LC-PUFA. The content of saturated fatty acid having 24 carbon atoms in the microbial oil is preferably at most 3.0% by weight, more preferably at most 1.0% by weight, and even more preferably at most 0.1% by weight with respect to the total weight of the microbial oil from the perspective of the suppression of the clogging of piping in column chromatography and the perspective of the purification efficiency of the target LC-PUFA.

Examples of other separation target fatty acids include saturated or unsaturated fatty acids having a partition number from 2 less than up to 2 greater than the partition number of the polyunsaturated fatty acid and a number of carbon atoms different from the number of carbon atoms of the polyunsaturated fatty acid, where the partition number is an index related to separation in liquid chromatography and is determined from the number of carbon atoms and the number of double bonds of the fatty acid. Such other separation target fatty acids will be called separation target fatty acids having a PN difference of from −2 and at most 2 hereafter.

In a case in which the PN of one of two fatty acids to be contrasted is a number 2 less than, that is, −2, a number 1 less than, that is, −1, the same number, that is, 0, a number 1 greater than, that is, +1, or a number 2 greater than, that is, +2, the PN of the other fatty acid, the difference in the elution times of the two fatty acids to be compared cannot be considered sufficient in a case in which separation using liquid chromatography is performed, and separation by liquid chromatography may be considered to be in a difficult relationship. Therefore, a decrease in the contents of a separation target fatty acids having a PN difference of from −2 up to 2 is preferable from the perspective of the purification efficiency of the target LC-PUFA with a high content.

The partition number (PN) may be also called an equivalent carbon number (ECN). The partition number is an index which is empirically obtained from the rules of separation factors affecting the elution time in relation to the analysis of molecular species in reverse phase high-performance liquid chromatography, and the index is expressed by the following formula (I):

$$PN = [\text{number of carbon atoms}] - 2 \times [\text{number of double bonds}] \quad (I)$$

In formula (I), the number of carbon atoms refers to the number of carbon atoms of the fatty acid. However, in the present invention, the number of carbon atoms in formula (I) refers to the number of carbon atoms of the fatty acid in a case of a free fatty acid form and is an integer unique to each fatty acid. In this specification, the partition number will be called PN.

For example, in the case of DGLA (that is, C20:3), PN=20−2×3=14.

A separation target fatty acid having a PN difference of at least −2 and at most 2 is a saturated or unsaturated fatty acid having a number of carbon atoms differing from the number of carbon atoms of the target LC-PUFA, that is, a carbon number greater than or less than the carbon number of the target LC-PUFA, and an example is a saturated or unsaturated fatty acid having a smaller number of carbon numbers than the target LC-PUFA. A separation target fatty acid having a PN difference of at least −2 and at most 2 may be at least one selected from the group consisting of saturated fatty acids having 18 carbon atoms, monounsaturated fatty acids having 18 carbon atoms, diunsaturated fatty acids having 18 carbon atoms, triunsaturated fatty acids having 18 carbon atoms, and tetraunsaturated fatty acids having 18 carbon atoms.

The following are examples of combinations of the target LC-PUFA and separation target fatty acids in the microbial oil.

TABLE 1

| target LC-PUFA | | | |
|---|---|---|---|
| name | | PN | Separation target fatty acid |
| Eicosadienoic acid | C20:2 | 16 | C18:0, C18:1, C18:2 |
| Dihomo-γ-linolenic acid | C20:3 | 14 | C18:1, C18:2, C18:3 |
| Mead acid | C20:3 | 14 | C18:1, C18:2, C18:3 |
| Eicosatetraenoic acid | C20:4 | 12 | C18:2, C18:3, C18:4 |
| Arachidonic acid | C20:4 | 12 | C18:2, C18:3, C18:4 |
| Eicosapentaenoic acid | C20:5 | 10 | C18:3, C18:4 |
| Docosatetraenoic acid | C22:4 | 14 | C18:1, C18:2, C18:3 |
| Docosapentaenoic acid | C22:5 | 12 | C18:2, C18:3, C18:4 |
| Docosahexaenoic acid | C22:6 | 10 | C18:3, C18:4 |

From the perspective of efficiently obtaining a target LC-PUFA with a high content, the total content of separation target fatty acids having a PN difference of at least −2 and at most 2 in the microbial oil containing separation target fatty acids is, for example, more preferably at most 10.0% by weight, even more preferably at most 4.0% by weight, and even more preferably at most 0.7% by weight of the total weight of fatty acids in the oil. In the microbial oil, the total content of separation target fatty acids having a PN difference of at least −2 and at most 2 is preferably at most 15/100, more preferably at most 5/100, and even more preferably at most 1/100 of the content of the target LC-PUFA from the perspective of efficiently obtaining the target LC-PUFA. The total content of separation target fatty acids having a PN difference of at least −2 and at most 2 in the microbial oil is preferably at most 10.0% by weight, more preferably at most 4.0% by weight, and even more preferably at most 0.7% by weight with respect to the total weight of the microbial oil from the perspective of efficiently obtaining the target LC-PUFA.

For example, in a case in which the target LC-PUFA is a fatty acid with PN16, that is, eicosadienoic acid, the total content of separation target fatty acids having a PN difference of at least −2 and at most 2 such as C18:0 and C18:1 in the microbial oil is more preferably at most 10.0% by weight, even more preferably at most 4.0% by weight, and even more preferably at most 0.7% by weight of the total weight of fatty acids in the oil; preferably at most 15/100, more preferably at most 5/100, and even more preferably at most 1/100 of the content of the target LC-PUFA; and preferably at most 10.0% by weight, more preferably at most 4.0% by weight, and even more preferably at most 0.7% by weight with respect to the total weight of the microbial oil.

In a case in which the target LC-PUFA is a fatty acid with PN14, that is, DGLA, Mead acid, or docosatetraenoic acid, the total content of separation target fatty acids having a PN difference of at least −2 and at most 2 such as C18:1 and C18:2 in the microbial oil is more preferably at most 10.0% by weight, even more preferably at most 4.0% by weight, and even more preferably at most 0.7% by weight of the total weight of fatty acids in the oil; preferably at most 15/100, more preferably at most 5/100, and even more preferably at most 1/100 of the content of the target LC-PUFA; and preferably at most 10.0% by weight, more preferably at most 4.0% by weight, and even more preferably at most 0.7% by weight with respect to the total weight of the microbial oil.

In the case in which the target LC-PUFA is a fatty acid with PN12, that is, eicosatetraenoic acid, arachidonic acid, or docosapentaenoic acid, the total content of separation target fatty acids having a PN difference of at least −2 and at most 2 such as C18:2 and C18:3 in the microbial oil is more preferably at most 10.0% by weight, even more preferably at most 4.0% by weight, and even more preferably at most 0.7% by weight of the total weight of fatty acids in the oil; preferably at most 15/100, more preferably at most 5/100, and even more preferably at most 1/100 of the content of the target LC-PUFA; and preferably at most 10.0% by weight, more preferably at most 4.0% by weight, and even more preferably at most 0.7% by weight with respect to the total weight of the microbial oil.

In a case in which the target LC-PUFA is a fatty acid with PN10, that is, eicosapentaenoic acid or docosahexaenoic acid, the total content of separation target fatty acids having a PN difference of at least −2 and at most 2 such as C18:3 and C18:4 in the microbial oil is more preferably at most 10.0% by weight, even more preferably at most 4.0% by weight, and even more preferably at most 0.7% by weight of the total weight of fatty acids in the oil; preferably at most 15/100, more preferably at most 5/100, and even more preferably at most 1/100 of the content of the target LC-PUFA; and preferably at most 10.0% by weight, more preferably at most 4.0% by weight, and even more preferably at most 0.7% by weight with respect to the total weight of the microbial oil.

From the perspective of efficiently obtaining a target LC-PUFA such as eicosadienoic acid, DGLA, Mead acid, or eicosatetraenoic acid at a high content by reverse phase column chromatography, the content of monounsaturated fatty acid having 18 carbon atoms is preferably low in the microbial oil. The PN of a monounsaturated fatty acid having 18 carbon atoms is 2 greater than that of the target LC-PUFA in a case in which eicosadienoic acid, DGLA, Mead acid, or eicosatetraenoic acid is used as the target LC-PUFA. For example, the content of monounsaturated fatty acid having 18 carbon atoms in the microbial oil is more preferably at most 7.0% by weight, even more preferably at most 1.5% by weight, and even more preferably at most 0.4% by weight of the total weight of fatty acids in the oil from the perspective of the purification efficiency of the target LC-PUFA. The content of monounsaturated fatty acid having 18 carbon atoms in the microbial oil is preferably at most 10/100, more preferably at most 2/100, and even more preferably at most 0.5/100 of the content of the target LC-PUFA from the perspective of the purification efficiency of the target LC-PUFA. The content of monounsaturated fatty acid having 18 carbon atoms in the microbial oil is preferably at most 7.0% by weight, more preferably at most 1.5% by weight, and even more preferably at most 0.4% by weight with respect to the total weight of the microbial oil from the perspective of the purification efficiency of the target LC-PUFA.

From the perspective of efficiently obtaining a target LC-PUFA such as DGLA, Mead acid, eicosatetraenoic acid, arachidonic acid, docosatetraenoic acid, or docosapentaenoic acid with a high content by reverse phase column chromatography, the content of diunsaturated fatty acids having 18 carbon atoms is preferably low in the microbial oil. The PN of a diunsaturated fatty acid having 18 carbon atoms is equal to that of the target LC-PUFA in a case in which DGLA, Mead acid, eicosatetraenoic acid, arachidonic acid, docosatetraenoic acid, or docosapentaenoic acid is used as the target LC-PUFA. For example, the content of diunsaturated fatty acid having 18 carbon atoms in the microbial oil is more preferably at most 5.0% by weight, even more preferably at most 0.7% by weight, and even more preferably at most 0.4% by weight of the total weight of fatty acids in the oil from the perspective of the purification efficiency of the target LC-PUFA. The content of diunsaturated fatty acid having 18 carbon atoms in the microbial oil is preferably at most 7/100, more preferably at most 1/100, and even more preferably at most 0.5/100 of the content of the target LC-PUFA from the perspective of the purification efficiency of the target LC-PUFA. The content of diunsaturated fatty acid having 18 carbon atoms in the microbial oil is preferably at most 5.0% by weight, more preferably at most 0.7% by weight, and even more preferably at most 0.4% by weight with respect to the total weight of the microbial oil.

From the perspective of efficiently obtaining a target LC-PUFA such as DGLA, Mead acid, or docosatetraenoic acid with a high content by reverse phase column chromatography, the content of triunsaturated fatty acid having 18 carbon atoms is preferably low in the microbial oil. The PN of a triunsaturated fatty acid having 18 carbon atoms is 2 lower than that of the target LC-PUFA in a case in which DGLA, Mead acid, or docosatetraenoic acid is used as the target LC-PUFA. For example, the content of triunsaturated fatty acid having 18 carbon atoms in the microbial oil is more preferably at most 7.0% by weight, even more preferably at most 1.5% by weight, and even more preferably at most 0.4% by weight of the total weight of fatty acids in the oil from the perspective of the purification efficiency of the target LC-PUFA. The content of triunsaturated fatty acid having 18 carbon atoms in the microbial oil is preferably at most 10/100, more preferably at most 2/100, and even more preferably at most 0.5/100 of the content of the target LC-PUFA from the perspective of the purification efficiency of the target LC-PUFA. The content of triunsaturated fatty acid having 18 carbon atoms in the microbial oil is preferably at most 7.0% by weight, more preferably at most 1.5% by weight, and even more preferably at most 0.4% by weight with respect to the total weight of the microbial oil from the perspective of the purification efficiency of the target LC-PUFA.

From the perspective of efficiently obtaining a target LC-PUFA such as DGLA, Mead acid, or docosatetraenoic acid with a high content by reverse phase column chromatography, the total content of monounsaturated fatty acid having 18 carbon atoms and diunsaturated fatty acid having 18 carbon atoms is preferably low in the microbial oil. For example, the total content of monounsaturated fatty acid having 18 carbon atoms and diunsaturated fatty acid having 18 carbon atoms in the microbial oil is more preferably at most 10.0% by weight, even more preferably at most 4.0% by weight, and even more preferably at most 0.7% by weight of the total weight of fatty acids in the oil from the perspective of efficiently obtaining the target LC-PUFA. The total content of monounsaturated fatty acid having 18 carbon atoms and diunsaturated fatty acid having 18 carbon atoms in the microbial oil is preferably at most 15/100, more preferably at most 5/100, and even more preferably at most 1/100 of the content of the target LC-PUFA from the perspective of efficiently obtaining the target LC-PUFA. The total content of monounsaturated fatty acid having 18 carbon atoms and diunsaturated fatty acid having 18 carbon atoms in the microbial oil is preferably at most 10.0% by weight, more preferably at most 4.0% by weight, and even more preferably at most 0.7% by weight with respect to the total weight of the microbial oil from the perspective of efficiently obtaining the target LC-PUFA.

The microbial oil of the present invention preferably has a low content of saturated fatty acid having 18 carbon atoms from the perspectives of the melting point of the microbial oil, the ease of crystal precipitation, and the time productivity in column chromatography. In a case in which eicosadienoic acid is used as the target LC-PUFA, saturated fatty acid having 18 carbon atoms also falls into the category of separation target fatty acids having a PN difference of at least −2 and at most 2. The content of saturated fatty acid having 18 carbon atoms in the microbial oil is preferably at most 7.0% by weight, more preferably at most 3.0% by weight, and even more preferably at most 1.5% by weight of the total weight of fatty acids in the oil from the perspectives of the melting point of the microbial oil, the ease of crystal precipitation, and the time productivity in column chromatography. The content of monounsaturated fatty acid having 18 carbon atoms in the microbial oil is preferably at most 11/100, more preferably at most 4/100, and even more preferably at most 2/100 of the content of the target LC-PUFA. The content of saturated fatty acid having 18 carbon atoms in the microbial oil is preferably at most 7.0% by weight, more preferably at most 3.0% by weight, and even more preferably at most 1.5% by weight with respect to the total weight of the microbial oil from the perspectives of the melting point of the microbial oil, the ease of crystal precipitation, and the time productivity in column chromatography.

The various contents of the separation target fatty acids described above respectively correspond to independent embodiments, so a preferred embodiment of the microbial oil may have an embodiment combining any two or more preferable contents of each of the separation target fatty acids.

In a case in which the target LC-PUFA in the microbial oil is eicosadienoic acid, DGLA, Mead acid, eicosatetraenoic acid, arachidonic acid, eicosapentaenoic acid, docosatetraenoic acid, docosapentaenoic acid, or docosahexaenoic acid, the total content of saturated fatty acid having 22 carbon atoms and saturated fatty acid having 24 carbon atoms in the microbial oil described above may be set within the same ranges as the ranges described above, including the preferred ranges, and may be combined as desired with each other, and may be combined with the descriptions of the content of monounsaturated fatty acid having 18 carbon atoms, the content of diunsaturated fatty acid having 18 carbon atoms, the total content of monounsaturated fatty acid having 18 carbon atoms and diunsaturated fatty acid having 18 carbon atoms, and the content of saturated fatty acid having 18 carbon atoms, for each target LC-PUFA as desired.

The melting point of the microbial oil is preferably at most 40° C. and more preferably at most 30° C. from the perspective of the treatment efficiency of reverse phase column chromatography or the packing heat resistance. The melting point of the microbial oil is the transparent melting point measured in accordance with the method described in "The JOCS Standard Methods for the Analysis of Fats, Oils and Related Materials", 2013 Edition, 3.2.2.1-2013 established by the Japan Oil Chemists' Society (JOCS).

(2) Production Method for Microbial Oil

The production methods for a microbial oil according to other aspects of the present invention all comprise: performing purification by rectification; and obtaining a specific microbial oil after rectification.

That is, the first production method for a microbial oil according to another aspect of the present invention comprises: a starting oil-providing process of providing a starting oil containing a target LC-PUFA obtained from microbial biomass; and a first rectification process of performing purification on the starting oil by rectification under conditions including a column bottom temperature of from 160° C. to 230° C. and a minimum pressure in the distillation column of from 0.1 Pa to 30 Pa. After the first rectification process, a microbial oil containing a specific polyunsaturated fatty acid is obtained. The specific polyunsaturated fatty acid obtained here includes, but is not limited to, a specific microbial oil of an aspect of the present invention.

The second production method for a microbial oil according to another aspect of the present invention comprises: the starting oil-providing process described above; a second rectification process of performing rectification on the starting oil using a distillation column containing structured packing under conditions including a column bottom temperature of from 160° C. to 230° C. and a minimum pressure in the distillation column of from 0.1 Pa to 30 Pa; and a microbial oil recovery process of obtaining the specific microbial oil of an aspect of the present invention.

The third production method for a microbial oil according to another aspect of the present invention comprises: the starting oil-providing process described above; a third rectification process of performing rectification on the starting oil using a distillation column containing structured packing under conditions including a column bottom temperature and a minimum pressure in the distillation column corresponding to the kind of the target polyunsaturated fatty acid, wherein a microbial oil containing thermally-produced fatty acid with a content of at most 3.0% by weight of the total weight of fatty acids in the oil may be obtained; and the microbial oil recovery process described above.

In the starting oil providing processes of the first to third production methods, the starting oil is obtained by a process of obtaining microbial biomass containing fatty acids by culturing a known microbe in a culture liquid as a lipid-producing microbe capable of producing a target LC-PUFA; a crude oil separation process of separating a crude oil as a mixture of fatty acids from the obtained microbial biomass; a triacylglycerol concentrated product production process of obtaining a triacylglycerol concentrated product by performing treatment including a degumming process, a deacidification (neutralization) process, a decoloration process, and a deodorization (bleaching) process on the crude oil in order to remove substances other than the target product, such as phospholipids and sterols; and a processing process of performing processing such as hydrolysis or alkyl esterification on the triacylglycerol concentrated product.

Examples of lipid-producing microbes include the microbes described above. In addition, the culturing of the lipid-producing microbe may be performed under conditions known to the person of ordinary skill in the art. For example, in a case in which the target LC-PUFA is DGLA, the DGLA may be derived from the microbe described in JP A No. H05-091887.

JP-A-No. H05-091887 discloses a method for producing DGLA by culturing the mutant strain *Mortierella alpina* SAM 1860 (Accession Number 3589 at the Fermentation Research Institute), induced by the reduction or loss of Δ5 desaturase activity, in the presence of a Δ5 desaturase inhibitor. Examples of Δ5 desaturase inhibitors include 2-amino-N-(3-chlorophenyl)benzamide, dioxabicyclo[3.3.0]octane derivatives, piperonyl butoxide, curcumin, and the like. Of these, the dioxabicyclo[3.3.0]octane derivative is exemplified by sesamin, sesaminol, episesamin, episesaminol, sesamolin, 2-(3,4-methylenedioxyphenyl)-6-(3-methoxy-4-hydroxyphenyl)-3,7-dioxabicyclo[3.3.0]octane, 2,6-bis-(3-methoxy-4-hydroxyphenyl)-3,7-dioxabicyclo[3.3.0]octane, 2-(3,4-methylenedioxyphenyl)-6-(3-methoxy-4-hydroxyphenoxy)-3,7-dioxabicyclo[3.3.0]octane, and the like.

No particular limitation is placed on the culture vessel used for culturing, and any device that is ordinarily used for the culturing of microbes can be used. For example, a culture vessel which enables liquid culturing at a scale of from 1 L to 50 L may be exemplified, and the culture vessel may be selected appropriately according to the scale of culturing. For example, in the case of liquid culturing at a scale of from 1 L to 50 L, a stirred-type culture vessel is preferably used as a culture vessel in order to obtain the target LC-PUFA at a higher concentration. The stirred-type culture vessel preferably has disc turbine-type agitator blades in at least one stage, and a stirred-type culture vessel further preferably has disc turbine type agitator blades in two stages.

In the crude oil separation process, a crude oil containing lipids produced in the production process is separated from the microbial biomass. For the separation of the microbial biomass and the collection of the crude oil, a separation method and an extraction method suited to the culturing form may be used.

In a case in which a liquid culture medium is used, a cultured cell is obtained by conventional solid-liquid separation means such as centrifugation and filtration. In a case in which a solid culture medium is used for culturing, the solid culture medium and microbial biomass may be crushed using a homogenizer or the like without separating the microbial biomass from the culture medium, and the crude oil may be collected directly from the crushed material.

The collection of the crude oil may comprise extracting the dried separated microbial biomass, preferably with supercritical carbon dioxide or with an organic solvent under a nitrogen gas stream. Examples of the organic solvents include ethers such as dimethylether and diethylether; hydrocarbons having at most 10 carbon atoms such as petroleum ether, hexane, and heptane; alcohols such as methanol and ethanol; chloroform; dichloromethane; fatty acids such as octanoic acid or alkyl esters thereof; and oils such as vegetable oil. Alternatively, good extraction results may be obtained by alternating extraction using methanol and petroleum ether, or extraction using a single layer-type solvent of chloroform-methanol-water. A crude oil containing a high concentration of fatty acids is obtained by distilling off the organic solvent from the extract under reduced pressure. Hexane is most generally used in the case of collecting triacylglycerol.

Moreover, as an alternative to the aforementioned method, extraction may be performed using moist microbial biomass. The collection of the crude oil from moist microbial biomass may be performed by compressing the moist microbial biomass or by using a solvent compatible with water such as methanol or ethanol, or a mixed solvent formed from a solvent compatible with water and water and/or another solvent. The remainder of the procedure is similar to that described above.

In the triacylglycerol concentrated product production process, degumming, deacidification, bleaching (decoloration) and deodorization are performed on the collected crude oil with methods used for the purification of vegetable oil, fish oil, and the like using methods known to those of ordinary skill in the art. For example, degumming treatment is performed by water-washing treatment; deacidification treatment is performed by distillation treatment; decoloration treatment is performed by decoloration treatment using activated clay, activated carbon, silica gel, or the like; and deodorization treatment is performed by steam (water vapor) distillation.

In the processing process, processing treatment such as esterification or hydrolysis using a catalyst, for example, is performed on the triacylglycerol concentrated product. Alkyl esterification treatment and hydrolysis treatment may be performed under conditions known to those of ordinary skill in the art.

For example, methyl esters of the fatty acids are obtained by treatment of the triacylglycerol concentrated product at room temperature for 1 to 24 hours using from 5% to 10% anhydrous methanol-hydrochloric acid, from 10% to 50% $BF_3$-methanol, or the like. The ethyl esters of the fatty acids are obtained by treatment of the oil for 15 to 60 minutes at 25° C. to 100° C. using from 1% to 20% sulfuric acid ethanol or the like. The methyl esters or ethyl esters may be extracted from the reaction liquid using an organic solvent such as hexane, diethylether, or ethyl acetate. The extracted liquid is dried using anhydrous sodium sulfate or the like, and then the organic solvent is removed by distillation to obtain a composition mainly composed of fatty acid alkyl esters.

The first to third production methods for a microbial oil respectively comprise first to third rectification processes of performing rectification on the starting oil obtained in the starting oil supply process under specific conditions. By performing the first to third rectification processes, a specific target microbial oil such as a desired microbial oil containing a target LC-PUFA, for example, may be efficiently obtained with the production method for a microbial oil according to the present invention.

In the first rectification process in the first production method for a microbial oil, purification is performed on the starting oil by rectification under conditions including a column bottom temperature of from 160° C. to 230° C. and a minimum pressure in the distillation column of from 0.1 Pa to 30 Pa. By performing purification by rectification at a column temperature and a minimum pressure in the distillation column within these ranges, a specific desired unsaturated fatty acid such as a target LC-PUFA may be precisely and efficiently obtained.

Rectification is a technique known to those of ordinary skill in the art, wherein a portion of vapor generated under heating conditions is returned to the distillation column as a reflux, and components are separated with precision using the gas-liquid equilibrium between the vapor rising inside the column and the liquid sample.

The column bottom temperature refers to the temperature of the sample at the base inside the distillation column. In a case in which the column bottom temperature is less than 160° C., it is not possible to sufficiently separate fatty acids other than the target fatty acids, such as fatty acids other than the target LC-PUFA such as unsaturated fatty acids having 18 carbon atoms, for example. On the other hand, in a case in which the column bottom temperature exceeds 230° C., the content of thermally-produced fatty acids or the like becomes high, even in the case of rectification, and it tends to be impossible to efficiently obtain a microbial oil containing the target LC-PUFA with a high content. The column bottom temperature is preferably from 160° C. to 210° C. and more preferably from 160° C. to 200° C. from the perspective of separation efficiency.

The temperature at the top of the column is not particularly limited and may be, for example, from 80° C. to 160° C. and more preferably from 90° C. to 140° C.

The minimum pressure in the distillation column typically corresponds to the pressure at the top of the distillation column. In the case of a typical distillation column provided with a condenser and a vacuum pump at the top of the column, the pressure from the condenser to the vacuum pump at the top of the column at which the rising vapor, that is, the distillate, is liquefied indicates the minimum pressure in the distillation column. In a case in which the minimum pressure in the distillation column is higher than 30 Pa, the column bottom temperature increases to generate the vapor required for rectification, and as a result, the content of thermally-produced fatty acids tends to become high. Alternatively, a pressure loss occurs due to piping or packing ordinarily contained in the distillation column, so the minimum pressure in the distillation column may be set to 0.1 Pa or lower. The minimum pressure in the distillation column is more preferably from 0.1 Pa to 20 Pa from the perspective of suppressing the generation of thermally-produced fatty acids.

In the second rectification process in the second production method for a microbial oil, rectification is performed on the starting oil using a distillation column containing structured packing under conditions including a column bottom temperature of from 160° C. to 230° C. and a minimum pressure in the distillation column of from 0.1 Pa to 30 Pa. In the second rectification process, gas-liquid exchange may be achieved with very little pressure loss since rectification is performed using a distillation column containing structured packing. As a result, rectification may be performed relatively gently even under conditions including the same column bottom temperature and minimum pressure in the distillation column. Due to such relatively gentle rectification, the heating conditions for the starting oil may be mitigated, which makes it possible to effectively suppress the generation of thermally-produced fatty acids and to more efficiently obtain a microbial oil containing the target LC-PUFA at a high content.

Structured packing is packing known in this industry to be applied to distillation, and the packing is formed from a plurality of layers related to one another by a regularly repeating geometrical relationship. The material of the structured packing is not particularly limited as long as it is provided with a unique repeating shape, and the material may be a metal such as stainless steel, aluminum, nickel, copper, Hastelloy, or Monel; a resin such as polypropylene; a ceramic; or a carbon such as carbon steel or carbon fiber, or the like. The material of the structured packing may be selected appropriately in accordance with the heating conditions and pressure conditions of distillation.

From the perspective of effectively suppressing the generation of thermally-produced fatty acids and more efficiently obtaining a microbial oil containing the target LC-PUFA at a high content, the specific surface area per unit of the structured packing is preferably from 125 $m^2/m^3$ to 1700 $m^2/m^3$, more preferably from 125 $m^2/m^3$ to 900 $m^2/m^3$, and even more preferably from 200 $m^2/m^3$ to 800 $m^2/m^3$.

Examples of preferable structured packings include the following: Mellapak, Mellapak Plus, plastic Mellapak, Mellagrid, BX/CY packing, BX Plus, plastic BX (Gauze packing), Mellacarbon, DX/EX packing, Melladur, Sulzer Lab Packing EX, Nutter grid, and Kuehne Rombopak, from Sulzer Chemtech.

The column bottom temperature in the second rectification process refers to the temperature at the base inside the distillation column. In the case in which the column bottom temperature is less than 160° C., it may not be possible to sufficiently separate fatty acids other than the target LC-PUFA, such as unsaturated fatty acids having 18 carbon atoms. On the other hand, in the case in which the column bottom temperature exceeds 230° C., the content of thermally-produced fatty acids or the like becomes high, even in the case of rectification, and it may not be possible to efficiently obtain a microbial oil containing the target LC-PUFA at a high content. The column bottom temperature is preferably from 160° C. to 210° C. and more preferably from 160° C. to 200° C. from the perspective of separation efficiency.

The temperature at the top of the column in the second rectification process is not particularly limited and may be, for example, from 80° C. to 160° C. and more preferably from 90° C. to 140° C.

The minimum pressure in the distillation column in the second rectification process typically corresponds to the pressure at the top of the distillation column. In the case of a typical distillation column provided with a condenser and a vacuum pump at the top of the column, the pressure from the condenser to the vacuum pump at the top of the column at which the rising vapor, that is, distillate, is liquefied indicates the minimum pressure in the distillation column. In a case in which the minimum pressure in the distillation column is higher than 30 Pa, the column bottom temperature increases to generate the vapor required for rectification, and as a result, the content of thermally-produced fatty acids tends to become high. Alternatively, a pressure loss occurs due to piping or packing ordinarily contained in the distillation column, so the minimum pressure in the distillation column may be set to 0.1 Pa or lower. The minimum pressure in the distillation column is more preferably from 0.1 Pa to 20 Pa from the perspective of suppressing the generation of thermally-produced fatty acids.

In the third rectification process of the third production method for a microbial oil, rectification is performed on the starting oil using a distillation column containing structured packing under conditions including a column bottom temperature and a minimum pressure in the distillation column corresponding to the kind of the target polyunsaturated fatty acid, wherein a microbial oil containing thermally-produced fatty acid with a content of at most 3.0% by weight of the total weight of fatty acids in the oil may be obtained. The column bottom temperature and the minimum pressure in the distillation column corresponding to the kind of the target LC-PUFA in the third rectification satisfy the conditions under which a microbial oil containing thermally-produced fatty acids with a content of at most 3.0% by weight of the total weight of fatty acids in the oil may be obtained. The column bottom temperature and the minimum pressure in the distillation column corresponding to the kind of the target LC-PUFA may be optimized based on the content of thermally-produced fatty acids and may be appropriately set by the person of ordinary skill in the art based on the type, size, shape and the like of the distillation column used, the type, packing height and the like of the structured packing contained in the distillation column, and other conditions.

From the perspective of the purification efficiency of the target LC-PUFA and the suppression of the generation of thermally-produced fatty acids, the third rectification process is preferably performed at a column bottom temperature of from 160° C. to 230° C. and a minimum pressure in the distillation column of from 0.1 Pa to 30 Pa. The column bottom temperature in the third rectification process is more preferably from 160° C. to 210° C. and even more preferably from 160° C. to 200° C. The minimum pressure in the distillation column in the third rectification process is more preferably from 0.1 Pa to 20 Pa from the perspective of suppressing the generation of thermally-produced fatty acids. The minimum pressure in the distillation column in the third rectification typically corresponds to the pressure at the top of the distillation column. In the case of a typical distillation column provided with a condenser and a vacuum pump at the top of the column, the pressure from the condenser to the vacuum pump at the top of the column at which the rising vapor, that is, distillate, is liquefied indicates the minimum pressure in the distillation column. The temperature at the top of the column is not particularly limited and may be, for example, from 80° C. to 160° C. and more preferably from 90° C. to 140° C.

Alternatively, the conditions of rectification in the first to third rectification processes may not limited to the conditions described above. For example, in a case in which rectification is used, the rectification process is preferably carried out by distillation under a reduced pressure at the upper part of the distillation column of less than or equal to 10 mmHg (1,333 Pa), and temperature of the column bottom in the range of 165° C. to 210° C., preferably 170° C. to 195°

C., from the perspective of suppressing the denaturation of the oil by heating and increasing rectification efficiency. The pressure of the upper part of the distillation column is preferably as low as possible, and more preferably less than or equal to 0.1 mmHg (13.33 Pa). No particular limitation is placed on the temperature at the upper part of the column, and for example, this temperature may be set to less than or equal to 160° C.

Alternatively, any of the first to third rectification processes may comprise a plurality of cycles of rectification under mutually differing conditions for the column bottom temperature and the minimum pressure in the distillation column. This makes it possible to effectively separate different separation target fatty acids in each rectification. An example of mutually differing conditions for the column bottom temperature and the minimum pressure in the distillation column is a combination of two or more stages of rectification at different column bottom temperatures.

For example, the first to third rectification processes may comprise a low-temperature rectification process at a column bottom temperature of from 160° C. to 220° C. and a minimum pressure of from 0.1 Pa to 30 Pa in the distillation column and high-temperature rectification process at a column bottom temperature of from 170° C. to 230° C. and a minimum pressure of from 0.1 Pa to 30 Pa in the distillation column as a combination of rectification processes with mutually differing column bottom temperatures and minimum pressures in the distillation column.

By performing a low-temperature rectification process, fatty acid components with a comparatively smaller molecular weight than the target LC-PUFA, for example, fatty acid components having 18 carbon atoms, may be removed as an initial distillation and a microbial oil containing the target LC-PUFA may be obtained as a residue. The column bottom temperature in the low-temperature rectification process is preferably from 160° C. to 200° C. and more preferably from 160° C. to 190° C.

By performing a high-temperature rectification process, the content of at least either saturated fatty acid having 22 carbon atoms or saturated fatty acid having 24 carbon atoms, which may cause pipe clogging, may be reduced and pipe clogging may be suppressed on performing purification by reverse phase column chromatography. As a result, a microbial oil containing the target LC-PUFA at a high content may be efficiently obtained. The content of the residual saturated fatty acid having 22 or 24 carbon atoms in the high-temperature rectification process increases to a greater degree than in the low-temperature rectification process. The column bottom temperature in the high-temperature rectification process is preferably from 170° C. to 210° C. from the perspective of removing saturated fatty acid having 22 or 24 carbon atoms having an increased content and suppressing the formation of thermally-produced fatty acid.

With regard to the temperature difference between the column bottom temperature in the low-temperature rectification process and that of the high-temperature rectification process, the column bottom temperature in the high-temperature rectification process is preferably from 3° C. to 20° C. higher and more preferably from 3° C. to 10° C. higher than the column bottom temperature in the low-temperature rectification process from the perspectives of the suppression of the thermally-produced fatty acid and the necessity to generate vapor from a residue having a high content of saturated fatty acids having 22 carbon atoms and 24 carbon atoms in the high-temperature rectification process.

In both the low-temperature rectification process and the high-temperature rectification process, the minimum pressure in the distillation column is more preferably from 0.1 Pa to 20 Pa and even more preferably from 0.1 Pa to 10 Pa from the perspective of suppressing the production of thermally-produced fatty acid. No particular limitation is placed on the temperature at the upper part of the column, for example, this temperature may be set to less than or equal to 160° C.

An appropriate heating time can be set by the person of ordinary skill in the art based on the descriptions of the working examples in this specification in accordance with the charged amount of the starting material composition for distillation.

Either the low-temperature rectification process or the high-temperature rectification process may be performed first. For example, by performing the high-temperature rectification process after the low-temperature rectification process, fatty acid components with a comparatively larger molecular weight than the target LC-PUFA may be removed as a residue, and a microbial oil from which both fatty acid components with a comparatively smaller molecular weight than the target LC-PUFA and fatty acid components with a comparatively larger molecular weight than the target LC-PUFA have been removed as distillates may be obtained.

In the microbial recovery process in the second and third rectification processes, a microbial oil containing the target LC-PUFA at a high content as a distillate obtained by the rectification processes may be recovered. Such a microbial oil is a concentrated microbial oil of the target LC-PUFA and is useful for efficiently obtaining the target LC-PUFA in the free fatty acid form and/or the alkyl ester form using reverse phase column chromatography.

(3) Concentrated Microbial Oil

In the concentrated microbial oil of an aspect of the present invention, the content of the target LC-PUFA is from 90% by weight to 98% by weight of the total weight of fatty acids in the oil; the content of thermally-produced fatty acid is from 0.0001% by weight to 3.0% by weight of the total weight of fatty acids in the oil; the total content of saturated fatty acid having 24 carbon atoms and saturated fatty acid having 22 carbon atoms is at most 1.0% by weight of the total weight of fatty acids in the oil; and the content of monounsaturated fatty acid having 18 carbon atoms is at most 5.0% by weight of the total weight of fatty acids in the oil.

For example, an example of a concentrated microbial oil is one in which the content of DGLA is from 90% by weight to 98% by weight of the total weight of fatty acids in the oil; the content of the thermally-produced fatty acid is from 0.0001% by weight to 3.0% by weight of the total weight of fatty acids in the oil; the total content of saturated fatty acid having 24 carbon atoms and saturated fatty acid having 22 carbon atoms is at most 1.0% by weight of the total weight of fatty acids in the oil; and the content of monounsaturated fatty acid having 18 carbon atoms is at most 5.0% by weight of the total weight of fatty acids in the oil.

In the concentrated microbial oil, the content of the target LC-PUFA is preferably from 90% by weight to 98% by weight, from 95% by weight to 98% by weight, from 96% by weight to 98% by weight, or from 97% by weight to 98% by weight of the total weight of fatty acids in the oil; the content of thermally-produced fatty acid is preferably from 0.01% by weight to 3.0% by weight, from 0.1% by weight to 3.0% by weight, from 0.1% by weight to 2.8% by weight, from 0.1% by weight to 2.5% by weight, from 0.1% by weight to 2.0% by weight, from 0.1% by weight to 1.5% by weight, from 0.1% by weight to 1.0% by weight, or from 0.1% by weight to 0.7% by weight of the total weight of fatty acids in the oil; the total content of saturated fatty acid having 24 carbon atoms and saturated fatty acid having 22 carbon atoms is preferably at most 1.0% by weight, at most 0.2% by weight, or 0% by weight of the total weight of fatty acids in the oil; and the content of monounsaturated fatty acid having 18 carbon atoms is preferably at most 5.0% by weight, at most 2.0% by weight, or 0% by weight of the total weight of fatty acids in the oil.

Alternatively, in another preferred concentrated microbial oil, the content of DGLA is preferably from 90% by weight to 98% by weight, from 95% by weight to 98% by weight, from 96% by weight to 98% by weight, or from 97% by weight to 98% by weight of the total weight of fatty acids in the oil; the content of the thermally-produced fatty acid is preferably from 0.1% by weight to 3.0% by weight, from 0.1% by weight to 2.8% by weight, from 0.1% by weight to 2.5% by weight, from 0.1% by weight to 2.0% by weight, from 0.1% by weight to 1.5% by weight, from 0.1% by weight to 1.0% by weight, or from 0.1% by weight to 0.7% by weight of the total weight of fatty acids in the oil; the total content of saturated fatty acid having 24 carbon atoms and saturated fatty acid having 22 carbon atoms is preferably at most 1.0% by weight, at most 0.2% by weight, or 0% by weight of the total weight of fatty acids in the oil; and the content of monounsaturated fatty acid having 18 carbon atoms is preferably at most 5.0% by weight, at most 2.0% by weight, or 0% by weight of the total weight of fatty acids in the oil.

In another preferred concentrated microbial oil, the content of eicosadienoic acid, Mead acid, eicosatetraenoic acid, arachidonic acid, eicosapentaenoic acid, docosatetraenoic acid, docosapentaenoic acid, or docosahexaenoic acid is preferably from 90% by weight to 98% by weight, from 95% by weight to 98% by weight, from 96% by weight to 98% by weight, or from 97% by weight to 98% by weight of the total weight of fatty acids in the oil; the content of thermally-produced fatty acid is preferably from 0.1% by weight to 3.0% by weight, from 0.1% by weight to 2.8% by weight, from 0.1% by weight to 2.5% by weight, from 0.1% by weight to 2.0% by weight, from 0.1% by weight to 1.5% by weight, from 0.1% by weight to 1.0% by weight, or from 0.1% by weight to 0.7% by weight of the total weight of fatty acids in the oil; the total content of saturated fatty acid having 24 carbon atoms and saturated fatty acid having 22 carbon atoms is preferably at most 1.0% by weight, at most 0.2% by weight, or 0% by weight of the total weight of fatty acids in the oil; and the content of monounsaturated fatty acid having 18 carbon atoms (C18:1) is preferably at most 5.0% by weight, at most 2.0% by weight, or 0% by weight of the total weight of fatty acids in the oil.

These concentrated microbial oils contain the target LC-PUFA such as eicosadienoic acid, DGLA, Mead acid, eicosatetraenoic acid, arachidonic acid, eicosapentaenoic acid, docosatetraenoic acid, docosapentaenoic acid, or docosahexaenoic acid for example, at high content and are therefore extremely useful for applications in which the target LC-PUFA such as DGLA is required at a high content and with good productivity.

(4) Production Method for a Concentrated Microbial Oil

The production method for a concentrated microbial oil according to one aspect of the present invention comprises: obtaining a microbial oil containing a target LC-PUFA by one of the production methods described above; and performing concentration treatment on the obtained microbial oil using reverse phase column chromatography.

In a microbial oil obtained by the production methods for a microbial oil according to any one of the aspects of the present invention described above, the content of the target LC-PUFA is high, and the content of fatty acids that are difficult to separate from the target LC-PUFA by reverse phase column chromatography is low, so the target LC-PUFA may be obtained efficiently and with a high content.

The reverse phase column chromatography used in concentration treatment may be a type of reverse phase column chromatography that is known in this industry, and high-performance liquid chromatography (HPLC) using a substrate modified by octadecylsilyl groups (ODS) as stationary phase is particularly preferable. An example of a reverse phase distribution column is a YMC pack ODS-AQ-HG column (YMC Co., Ltd.).

Examples of the HPLC conditions applied to concentration treatment are as follows.

Column: YMC pack ODS-AQ-HG 20 mm φ×500 mm (YMC Co., Ltd.)

Pump: 1200 Series G1361A Prep Pump (Agilent Technologies)

Column temperature: around 21° C.

Mobile phase: 17.5 mL/min of methanol

Sample conditions: load: 2.4 g, that is, the starting material load ratio is 3% by weight with respect to an adsorbent.

By using a microbial oil of the aforementioned aspects of the present invention, the recovery rate of the target LC-PUFA in reverse phase column chromatography may be preferably at least 50%, more preferably at least 80%, and even more preferably at least 90%.

The microbial oils and concentrated microbial oils according to the aspects of the present invention and the microbial oils and concentrated microbial oils obtained by the production methods of the aspects of the present invention contain or may contain the target LC-PUFA at a high content, and do not comprise components that may be mixed into the oils as a result of using separation means other than rectification. Examples of components that may be mixed into the oils as a result of using separation means other than rectification include metals such as silver, large quantities of urea, and the like.

Therefore, microbial oils and concentrated microbial oils according to the aspects of the present invention are extremely useful for applications in which the target LC-PUFA such as DGLA is required at a high content and with good productivity. Examples of such applications include usage in food products, supplements, medicaments, cosmetics, animal foods, and the like and usage in the production methods thereof. In particular, such applications include medicaments containing microbial oils and concentrated microbial oils containing target LC-PUFA as active components. For example, in the case of DGLA, applications targeting the functionality of DGLA are particularly preferred, and such applications are exemplified by anti-inflammatory applications, anti-allergy applications, and the like.

(5) Agent for Preventing or Treating Inflammatory Disease

A microbial oil or a concentrated microbial oil according to the aspects of the present invention contains the target LC-PUFA such as DGLA as an active component based on the functionality of the target LC-PUFA such as DGLA, and may therefore be comprised in an agent for preventing or treating an inflammatory disease. That is, the agent for preventing or treating inflammatory disease according to an aspect of the present invention comprises the microbial oil or concentrated microbial oil of another aspect of the present invention as an active component. The agent for preventing or treating inflammatory disease may be for example an anti-inflammatory agent, an anti-allergic agent, or the like.

Specifically, inflammatory disease includes skin inflammation. Skin inflammation may be at least one selected from the group consisting of rashes, hives, blisters, wheals and eczema, or may be caused by at least one selected from the group consisting of exposure to radiation, autoimmune diseases and uremic pruritus.

In particular the skin inflammation may be skin inflammation associated with or caused by atopic eczema, contact dermatitis, psoriasis or uremic pruritus.

The term eczema is applied to a wide range of skin conditions with a variety of aetiologies. In general, eczema is characterized by inflammation of the epidermis. Common symptoms associated with eczema include dryness, recurring skin rashes, redness, skin edema (swelling), itching, crusting, flaking, blistering, cracking, oozing, and bleeding. Eczema includes atopic eczema (atopic dermatitis), contact dermatitis, xerotic eczema, seborrhoeic dermatitis, dyshydrosis, discoid eczema, venous eczema, dermatitis herpetiformus, neurodermatitis and autoeczematisation. Eczema is typically atopic eczema or contact dermatitis.

Atopic eczema is primarily aggravated by contact with or intake of allergens, which include animal hair and dander, food allergens, for example nuts or shellfish, and drugs, for example penicillin.

Contact dermatitis includes allergic contact dermatitis, irritant contact dermatitis and photocontact dermatitis. Photocontact dermatitis includes phototoxic contact dermatitis and photoallergic contact dermatitis.

The skin inflammation may be skin inflammation caused by exposure of the skin to electromagnetic radiation. This includes, for example, exposure to sunlight, heat, X-rays or radioactive materials. Thus, the medicament may be used to treat sunburn.

Electromagnetic radiation includes radio waves, microwaves, terahertz radiation, infrared radiation, visible light, ultraviolet radiation, X-rays and gamma rays. Electromagnetic radiation is preferably infrared radiation, visible light, ultraviolet radiation, X-rays and gamma rays, more preferably ultraviolet radiation, X-rays and gamma rays.

Autoimmune diseases may involve an autoimmune response against the skin. Examples of such autoimmune diseases are lupus and psoriasis.

Uremic pruritus is a disorder of the skin associated with chronic renal failure. It also frequently affects patients undergoing dialysis treatment.

Optionally the microbial oil or the concentrated microbial oil according to the other aspect of the invention is used co-administered with a corticosteroid or other therapeutic agent for any of the above medical uses.

In other aspects of the invention, the inflammatory disease may be at least one of the group consisting of atopic dermatitis, allergic contact dermatitis (ACD), irritant contact dermatitis (ICD), photocontact dermatitis, systemic contact dermatitis, rheumatism, psoriasis, lupus.

The agent for preventing or treating an inflammatory disease may be administered to a subject suffering from, or at risk of suffering from, an inflammatory disease. An administering form, the agent may be administered by orally or topically. The agent for treating an inflammatory disease is a medicament which is to suppress or relieve one or more symptoms when the symptom(s) is/are found due to inflammatory disease. On the other hand, the agent for prevention of inflammatory disease is a medicament to suppress, by pre-administration, an occurrence of one or more symptoms which may be predicted or anticipated due to inflammatory disease. However, the terms "agent for treating an inflammatory disease" and "agent for preventing an inflammatory disease" should be understood taking into account multiple or general aspects such as the timing of use or the symptom(s) on use, and should not be restrictively applied.

Another aspect of the present invention provides a method for prevention, treatment or amelioration of an inflammatory disease, the method comprising: administering the agent for preventing or treating an inflammatory disease described herein to a subject suffering from, or at risk of suffering from, the inflammatory disease. As an administering form, the agent may be administered orally or topically.

The microbial oil of the present invention may contain each component at a content based on the area % thereof in accordance with column chromatography analysis. That is, each aspect of the present invention further provides the following microbial oil, a production method for a microbial oil, a concentrated microbial oil, and a production method for a concentrated microbial oil.

<1> A microbial oil containing:
at least one polyunsaturated fatty acid having at least 20 carbon atoms in fatty acid alkyl ester form and/or free fatty acid form at a content of at least 50 area % of the total area of fatty acids in the oil as measured by gas chromatography; and
thermally-produced fatty acid having from 16 to 22 carbon atoms at a content of at most 3.0 area % of the total area of fatty acids in the oil as measured by gas chromatography.

<2> The microbial oil of <1>, wherein the content of the polyunsaturated fatty acid is from 80 area % to 98 area % of the total area of fatty acids in the oil as measured by gas chromatography.

<3> The microbial oil of <1> or <2>, wherein the content of thermally-produced fatty acid is from 0.0001 area % to 3.0 area % of the total area of fatty acids in the oil as measured by gas chromatography.

<4> The microbial oil of any one of <1> to <3>, wherein a total content of saturated fatty acid having 22 carbon atoms and saturated fatty acid having 24 carbon atoms is at most 6.0 area % of the total area of fatty acids in the oil as measured by gas chromatography.

<5> The microbial oil of any one of <1> to <4>, wherein a total content of saturated fatty acid having 22 carbon atoms and saturated fatty acid having 24 carbon atoms is at most 10/100 of the content of the polyunsaturated fatty acid.

<6> The microbial oil of any one of <1> to <5>, wherein a content of saturated fatty acid having 24 carbon atoms is at most 3.0 area % of the total area of fatty acids in the oil as measured by gas chromatography.

<7> The microbial oil of any one of <1> to <6>, wherein a the content of saturated fatty acid having 24 carbon atoms is at most 4/100 of the content of the polyunsaturated fatty acid.

<8> The microbial oil of any one of <1> to <7>, wherein the microbial oil has a content of other saturated fatty acid, having a partition number from 2 less than up to 2 greater than that of said polyunsaturated fatty acid and a number of carbon atoms different from the number of carbon atoms of said polyunsaturated fatty acid, of at most 10.0 area % of the total area of fatty acids in the oil as measured by gas chromatography, wherein the partition number used is an index related to separation in liquid chromatography and is determined from the number of carbon atoms and the number of double bonds of a fatty acid.

<9> The microbial oil of <8>, wherein a content of the other saturated or unsaturated fatty acids is at most 15/100 of the content of the polyunsaturated fatty acid.

<10> The microbial oil of anyone of <1> to <9>, wherein the polyunsaturated fatty acid is at least one selected from the group consisting of eicosadienoic acid, dihomo-γ-linolenic acid, Mead acid, eicosatetraenoic acid, arachidonic acid, eicosapentaenoic acid, docosatetraenoic acid, docosapentaenoic acid, and docosahexaenoic acid.

<11> The microbial oil of any one of <8> to <10>, wherein the other saturated or unsaturated fatty acid comprises at least one selected from the group consisting of saturated fatty acids having 18 carbon atoms, monounsaturated fatty acids having 18 carbon atoms, diunsaturated fatty acids having 18 carbon atoms, triunsaturated fatty acids having 18 carbon atoms, and tetraunsaturated fatty acids having 18 carbon atoms.

<12> The microbial oil of any one of <1> to <11>, wherein the polyunsaturated fatty acid is dihomo-γ-linolenic acid, and the thermally-produced fatty acid is thermally-produced fatty acid having 20 carbon atoms.

<13> The microbial oil of <12>, wherein the thermally-produced fatty acid comprises at least one of a first substance having a retention time with a peak appearing within a range of from 1.001 to 1.011 and a second substance having a retention time with a peak appearing within a range of from 1.013 to 1.027 in gas chromatography analysis performed under the following conditions on an ethyl ester of the thermally-produced fatty acid, where the retention time of ethyl dihomo-γ-linolenate is defined as 1:
Device: 6890N Network GC system (Agilent Technologies)
Column: DB-WAX, length 30 m×inside diameter 0.25 mm×film thickness 0.25 μm (Agilent Technologies)
Column temperature conditions: 2.5 minutes at 60° C.→heated at 20° C./min→180° C.→heating at 2° C./min→15 minutes at 230° C.
Inlet temperature conditions: 210° C., splitless, split vent sampling time 1.5 min, purge flow rate 40 mL/min
Injection conditions: injection volume 1 μL, sample concentration 1 mg/mL or less
Detector: FID
Detector temperature: 280° C.
Carrier gas conditions: helium, linear velocity 24 cm/min.

<14> The microbial oil of <13>, wherein the polyunsaturated fatty acid is dihomo-γ-linolenic acid, and the total content of the first substance and the second substance is from 0.001 area % to 2.8 area % of the total area of fatty acids in the oil as measured by gas chromatography.

<15> The microbial oil of any one of <10> to <14>, wherein the content of monounsaturated fatty acids having 18 carbon atoms is at most 7.0 area % of the total area of fatty acids in the oil as measured by gas chromatography.

<16> The microbial oil of any one of <10> to <15>, wherein the content of monounsaturated fatty acid having 18 carbon atoms is at most 10/100 of the content of the polyunsaturated fatty acid.

<17> The microbial oil of any one of <10> to <16>, wherein the content of diunsaturated fatty acid having 18 carbon atoms is at most 7/100 of the content of the polyunsaturated fatty acid.

<18> The microbial oil of any one of <10> to <17>, wherein the total content of monounsaturated fatty acid having 18 carbon atoms and diunsaturated fatty acids having 18 carbon atoms is at most 15/100 of the content of the polyunsaturated fatty acid.

<19> The microbial oil of any one of <10> to <18>, wherein the content of saturated fatty acid having 18 carbon atoms is at most 11/100 of the content of the polyunsaturated fatty acid.

<20> A production method for microbial oil comprising:
providing a starting oil containing at least one polyunsaturated fatty acid having at least 20 carbon atoms in alkyl ester form and/or in free fatty acid form, obtained from microbial biomass; and
performing a purification on the starting oil by rectification under conditions including a column bottom temperature of from 160° C. to 230° C. and a minimum pressure in the distillation column of from 0.1 Pa to 30 Pa.

<21> A production method for microbial oil comprising:
providing a starting oil containing at least one polyunsaturated fatty acid having at least 20 carbon atoms in alkyl ester form and/or in free fatty acid form, obtained from microbial biomass;
performing a rectification on the starting oil by rectification using a distillation column containing structured packing under conditions including a column bottom temperature of from 160° C. to 230° C. and a minimum pressure in the distillation column of from 0.1 Pa to 30 Pa; and
obtaining a microbial oil of any one of <1> to <19>.

<22> A production method for microbial oil comprising:
providing a starting oil containing at least one polyunsaturated fatty acid having at least 20 carbon atoms in alkyl ester form and/or in free fatty acid form, obtained from microbial biomass;
performing rectification on the starting oil using a distillation column containing structured packing under conditions including a column bottom temperature and a minimum pressure in the distillation column corresponding to the kind of the target polyunsaturated fatty acid, wherein microbial oil containing thermally-produced fatty acid having from 16 to 22 carbon atoms at a content of at most 3.0 area % of the total area of fatty acids in the oil as measured by gas chromatography may be obtained; and
obtaining a microbial oil of any one of <1> to <19>.

<23> The production method of <22>, wherein the rectification is performed at a column bottom temperature of from 160° C. to 230° C. and a minimum pressure in the distillation column of from 0.1 Pa to 30 Pa.

<24> The production method of any one of <20> to <23>, wherein the rectification comprises a plurality of cycles of rectification under mutually differing conditions for the column bottom temperature and column top pressure.

<25> The production method of <24>, wherein the rectification comprises low-temperature rectification at a column bottom temperature of from 160° C. to 220° C. and a minimum pressure in the distillation column of from 0.1 Pa to 30 Pa; and high-temperature rectification at a column bottom temperature of from 170° C. to 230° C. and a minimum pressure in the distillation column of from 0.1 Pa to 30 Pa.

<26> The production method of <25>, wherein the column bottom temperature in the high-temperature rectification is from 3° C. to 20° C. higher than the column bottom temperature of the low-temperature rectification.

<27> The production method of any one of <21> to <26>, wherein the specific surface area per unit of the structured packing is from 125 m²/m³ to 1700 m²/m³.

<28> A concentrated microbial oil, the oil having:
a content of polyunsaturated fatty acid having at least 20 carbon atoms in fatty acid alkyl ester form and/or in free fatty acid form of from 90 area % to 98 area % of the total area of fatty acids in the oil as measured by gas chromatography;
a content of thermally-produced fatty acid having from 16 to 22 carbon atoms of from 0.0001 area % to 3.0 area % of the total area of fatty acids in the oil as measured by gas chromatography;
a total content of saturated fatty acid having 24 carbon atoms and saturated fatty acid having 22 carbon atoms of at most 1.0 area % of the total area of fatty acids in the oil as measured by gas chromatography; and
a content of monounsaturated fatty acid having 18 carbon atoms of at most 5.0 area % of the total area of fatty acids in the oil as measured by gas chromatography.

<29> A concentrated microbial oil, the oil having:
a content of dihomo-γ-linolenic acid in fatty acid alkyl ester form and/or in free fatty acid form of from 90 area % to 98 area % of the total area of fatty acids in the oil as measured by gas chromatography,
a content of thermally-produced fatty acid having from 16 to 22 carbon atoms of from 0.0001 area % to 3.0 area % of the total area of fatty acids in the oil as measured by gas chromatography;
a total content of saturated fatty acid having 24 carbon atoms and saturated fatty acid having 22 carbon atoms of at most 1.0 area % of the total area of fatty acids in the oil as measured by gas chromatography; and
a content of monounsaturated fatty acids having 18 carbon atoms of at most 5.0 area % of the total area of fatty acids in the oil as measured by gas chromatography.

<30> A production method for a concentrated microbial oil comprising:
obtaining a microbial oil containing at least one target polyunsaturated fatty acid having at least 20 carbon atoms in fatty acid alkyl ester form and/or in free fatty acid form, using a production method of any one of <20> to <27>; and
performing concentration treatment on the obtained microbial oil using reverse phase column chromatography.

<31> Use of a microbial oil of anyone of <1> to <19> or a concentrated microbial oil of <28> or <29> in a food product, supplement, medicament, cosmetic, or animal food.

<32> The use of a microbial oil of any one of <1> to <19> or a concentrated microbial oil of <28> or <29> in a production method for a food product, supplement, medicament, cosmetic, or animal food.

<33> A medicament containing a microbial oil of any one of <1> to <19> or a concentrated microbial oil of <28> or <29>.

<34> An agent for preventing or treating inflammatory disease comprising a microbial oil of any one of <1> to <19> or a concentrated microbial oil of <28> or <29>.

<35> The agent for preventing or treating inflammatory disease of <34>, wherein the agent is an anti-allergic agent or an anti-inflammatory agent.

<36> The agent for preventing or treating inflammatory disease of <34> or <35>, wherein the inflammatory disease is at least one skin inflammatory disease selected from the group consisting of rashes, hives, blisters, wheal, and eczema, or skin inflammatory disease caused by at least one selected from the group consisting of exposure to radiation, autoimmune disease, and uremic pruritus.

<37> The agent for preventing or treating inflammatory disease of <34> or <35>, wherein the skin inflammatory disease is at least one selected from the group consisting of atopic dermatitis, allergic contact dermatitis, irritant contact dermatitis, photocontact dermatitis, systemic contact dermatitis, rheumatism, psoriasis, and lupus.

<38> A method for prevention, treatment, or amelioration of inflammatory disease, the method comprising:
administering the agent for preventing or treating inflammatory disease of any one of <34> to <37> to a subject suffering from, or at risk of suffering from an inflammatory disease.

<39> A method for prevention, treatment or amelioration of an inflammatory disease of
<38>, wherein the administration is by oral administration or local administration.

<40> A microbial oil obtained by a production method of any one of <20> to <27>.

<41> A concentrated microbial oil obtained by a production method of <30>.

As described above, in the present invention, the contents of each component of the microbial oils and the concentrated microbial oils are the same when represented in terms of area % based on measurements by gas chromatography and when represented in terms of % by weight. Therefore, descriptions related to the contents of each component of the microbial oils and the concentrated microbial oils represented in terms of area % based on measurements by gas chromatography are established by directly replacing each of the numerical values represented in terms of % by weight with numerical values represented in terms of area %, and this applies throughout the entire text.

In addition, in this specification, the features of each invention described in embodiments related to each aspect of the invention may be combined as desired to form new embodiments, and it is to be understood that such new embodiments may be included in each of the aspects of the present invention.

EXAMPLES

The present invention is described below in detail using working examples. However, the present invention is not limited in any manner by these working examples. Unless specified otherwise, "%" is indicated on a mass basis.

In the working examples and the comparative examples of the following sections, the target LC-PUFA is DGLA in ethyl ester form, but the present invention is not limited to this case, and DGLA in free fatty acid form may be used as the target LC-PUFA, or another fatty acid in alkyl ester form or free fatty acid form may be used as the target LC-PUFA.

Experience shows that the ethyl esterification rate of the alkyl esterification method used in the working examples and the comparative examples of the following sections is from 95% to 100%. Therefore, in the example section, it was presumed that most of the saturated and unsaturated fatty acids contained in the obtained starting material ethyl ester were in the fatty acid ethyl ester form. Consequently, in the following comparative examples and working examples, the saturated and unsaturated fatty acids contained in the microbial oils are all described as saturated or unsaturated fatty acids in ethyl ester form.

In addition, hereafter, DGLA ethyl ester is simply expressed as "DGLA"; monounsaturated fatty acid ethyl ester having 18 carbon atoms is simply expressed as "C18:1"; diunsaturated fatty acid ethyl ester having 18 carbon atoms is simply expressed as "C18:2"; saturated fatty acid ethyl ester having 22 carbon atoms is simply expressed as "C22:0", and saturated fatty acid ethyl ester having 24 carbon atoms is simply expressed as "C24:0".

Comparative Example 1

A starting material ethyl ester 1 was prepared by performing ethyl esterification on a microbial oil 1 derived from a microbe of the genus *Mortierella* containing 37.2% by weight DGLA in the fatty acid composition with an alkaline catalyst in accordance with a conventional method. That is, 14 g of a 20% by weight sodium ethoxide-ethanol solution and 40 mL of ethanol were added to 120 g of the microbial oil 1 and the reaction liquid obtained was refluxed while heating in an oil bath for 2 hours. Next, the reaction liquid was air-cooled to a temperature of 40° C. or lower and then transferred to a separatory funnel. 400 mL of hexane was added to the reaction liquid transferred to the separatory funnel, and then purified water was added to wash by water. This water washing was repeated. After the washing water obtained after washing became neutral, washing with saturated saline was carried out once and the hexane layer was then recovered. Anhydrous sodium sulfate was added to the recovered hexane layer to dehydrate. The solvent was then removed by an evaporator and by vacuuming so as to obtain a starting material ethyl ester 1.

In the starting material ethyl ester 1 the DGLA content, that is the content of DGLA with respect to the obtained starting material ethyl ester, was 37.2% by weight. The weight ratio of C18:1 with respect to DGLA, that is, C18:1/DGLA, was 23.5/100. The weight ratio of C18:2, that is, C18:2/DGLA, was 17.8/100.

The starting material ethyl ester 1 was used in HPLC under the following conditions without performing distillation treatment so as to fractionate a DGLA eluted fraction.

In HPLC, the eluate was fractionated from the time that treatment was initiated by feeding the starting material ethyl ester 1 into the device until all fatty acids contained in the starting material ethyl ester 1 were completely eluted. One mL of each of the obtained fractions was collected exactly, and the solvent was then removed by an evaporator. The fraction remaining after the solvent was removed was dissolved in exactly 1 mL of methyl tricosanoate, that is, a 1.0 mg/mL hexane solution of C23:0 methyl ester, as an internal standard and was used as a measurement sample in gas chromatography (GC) under the conditions described below.

The amounts of fatty acids contained in the measurement sample and the fatty acid composition were determined from each of the fatty acid peak areas obtained in GC based on the following formula (II), and the DGLA content, that is, the content of DGLA with respect to the obtained fraction, and the recovery rate were further calculated. The recovery rate of DGLA was calculated by calculating the ratio of the total amount of DGLA in the recovered fraction with respect to the total amount of DGLA in all of the fractions in the fractionated HPLC eluate. The recovery rate was calculated with the same method below.

$$\text{Amount of fatty acids contained in the fraction [mg]} = \text{(peak area of each fatty acid} \times \text{fraction volume [mL])} / \text{(peak area of the } C23:0 \text{ methyl ester)} \times \text{added amount of the internal standard (1.0 mg)} \quad \text{(II)}$$

The results are shown in Table 2. As shown in Table 2, the DGLA content was 91.1% by weight, and the DGLA recovery rate was 8.1%. In Table 2, the numerical values in the "microbial oil" section of Comparative Example 1 are the numerical values for the starting material ethyl ester 1. All of the contents and weight ratios in Table 2 express the contents and weight ratios based on the fatty acid compositions. This is the same hereafter.

HPLC Conditions
  Column: YMC pack ODS-AQ-HG 20 mm φ×1000 mm (YMC Co., Ltd.). Two columns with a column length of 500 mm were connected in series.
  Pump: 1200 Series G1361A Prep Pump (Agilent Technologies)
  Column temperature: 40° C.
  Mobile phase: 35 mL/min of methanol
  Sample conditions: load 2.4 g, the material load factor is 3% by weight with respect to the packing GC Conditions
  Device: 6890N Network GC system (Agilent Technologies)
  Column: DB-WAX, length 30 m×inside diameter 0.25 mm×film thickness 0.25 μm (Agilent Technologies)
  Column temperature conditions: 180° C.→heated at 3° C./min→30 minutes at 230° C.
  Inlet temperature: 250° C.
  Detector: FID
  Detector temperature: 250° C.
  Carrier gas conditions: helium, linear velocity 30 cm/min
  Split conditions: split ratio=1:30, injection volume 1 μL, sample concentration 9 mg/mL Comparative Example 2

Short-path distillation (SPD) was performed on the starting material ethyl ester 1 used in Comparative Example 1 under the following conditions to remove fatty acid fractions having 18 carbon atoms or fewer.

A KDL-5 (UIC GmbH) was used as an SPD device. Under temperature and vacuum conditions with a starting material temperature of 40° C., an evaporation surface inlet heating medium temperature of 100° C., an outlet heating medium temperature of 87° C., an internal condenser temperature of 30° C., and pressure in front of the pump of 0.001 mbar, that is, 0.133 mPa, 160.7 g of the starting material was fed at 300 mL/h, and distillates containing large amounts of C18 or smaller fractions were removed to obtain 65.9 g of a residue. DGLA was contained in the residue in a concentrated state.

The obtained residue was used in HPLC under the following conditions to fractionate a DGLA eluted fraction. The DGLA eluted fraction corresponds to a concentrated microbial oil.

The amounts of fatty acids contained and the fatty acid composition were found for the obtained fraction after SPD treatment and the DGLA eluted fraction after HPLC treatment using gas chromatography in the same manner as in Comparative Example 1, and the DGLA content, that is, the content of DGLA with respect to the obtained fraction, and the recovery rate were further calculated. The results are shown in Table 2. As shown in Table 2, the DGLA content in the fraction after SPD treatment was 40.9% by weight; the DGLA content of the DGLA eluted fraction was 94.4% by weight; and the DGLA recovery rate was 5.1%.

HPLC Conditions
Column: YMC pack ODS-AQ-HG 20 mm φ×1000 mm (YMC Co., Ltd.). Two columns with a column length of 500 mm were connected in series.
Pump: 1200 Series G1361A Prep Pump (Agilent Technologies)
Column temperature: 40° C.
Mobile phase: 12 mL/min of methanol
Sample conditions: load 2.4 g, that is, the material load is 1.5% by weight with respect to the packing.

Working Example 1

A starting material ethyl ester 2 was prepared by performing ethyl esterification on a microbial oil 2 derived from a microbe of the genus *Mortierella* containing 32.8% by weight DGLA in the fatty acid composition with an alkaline catalyst in accordance with a conventional method. That is, 14 g of a 20% by weight sodium ethoxide-ethanol solution and 40 mL of ethanol were added to 120 g of the microbial oil 2, and the reaction liquid obtained was refluxed while heating in an oil bath for 2 hours. Next, the reaction liquid was air-cooled to a temperature of 40° C. or lower and then transferred to a separatory funnel. To the reaction liquid transferred to the separatory funnel, 400 mL of hexane was added and then purified water was added to wash by water. This water washing was repeated. After the washing water obtained after washing became neutral, the washing with saturated saline was carried out one time, and the hexane layer was then recovered. Anhydrous sodium sulfate was added to the recovered hexane layer to dehydrate. The solvent was then removed by an evaporator and by vacuuming so as to obtain a starting material ethyl ester 2.

In the starting material ethyl ester 2, the DGLA content, that is, the content of DGLA with respect to the obtained starting material ethyl ester, was 32.8% by weight. The weight ratio of C18:1 with respect to DGLA, that is, C18:1/DGLA, was 26.1/100. The weight ratio of C18:2 with respect to DGLA, that is, C18:2/DGLA, was 17.2/100.

The starting material ethyl ester 2 was used as a sample in rectification including the following low-temperature rectification process and high-temperature rectification process. In the low-temperature rectification process, the following rectification was performed on 100 g of the starting material ethyl ester 2. A fractioning column with a vacuum jacket (Kiriyama Glass) was used as a fractioning column, and five Sulzer Lab Packing EX units (Sulzer Chemtech) were used for internal packing. The diameter of the fractioning column with a vacuum jacket was 25 mm, and the size of each Sulzer Lab Packing EX unit was 25 mm×50 mm. Rectification was performed with a liquid temperature inside the column base oven, that is, the column bottom temperature, of 185° C., a column top vapor temperature, that is, the column top temperature, of 135° C., and a pressure in front of the vacuum pump, that is, the minimum pressure in the distillation column; i.e. the degree of vacuum, of 30 Pa. In the low-temperature rectification process, fractions of C18 and smaller were removed as initial distillates, and 40 g of a residue excluding the initial distillates was obtained. When the amounts of fatty acids and the fatty acid composition were confirmed for the residue excluding the initial distillates using the same gas chromatography as in Comparative Example 1, the DGLA ethyl ester was contained in a concentrated state in the residue excluding the initial distillates.

In addition, in a chromatogram of the residue excluding the initial distillates, a compound A indicated by a peak A that is not ordinarily observed in chromatograms using crude oils as samples appeared between a peak representing C20:3, n-6 (DGLA) and a peak representing C20:4, n-6 (see Table 3). In addition, a compound B indicated by peak B that is not ordinarily observed in chromatograms using crude oils as samples appeared near the peak representing C20:4, n-6. Compound A and compound B can be considered to be compounds formed by the distillation treatment and were assessed to be thermally-produced fatty acids. The contents of compound A and compound B are shown in Tables 2 and 3. The contents in Table 3 represent contents based on the fatty acid compositions.

In cases in which the fatty acids contained in the crude oil overlapped with the peaks of thermally-produced fatty acids under the GC conditions used in Comparative Example 1, in order to separate and quantify the compound A and the compound B, the fatty acids originally contained in the crude oil were removed by silver-ion solid phase extraction, and the resulting sample was then used in gas chromatography under the following conditions. In a case in which the retention time of ethyl dihomo-γ-linolenate was defined as 1, a compound having a retention time represented by a peak appearing within the range of from 1.001 to 1.009, that is, peak A, was identified as compound A. Similarly, a compound having a retention time represented by a peak appearing within the range of from 1.013 to 1.024, that is, peak B, was identified as compound B. The relative ratios of DGLA, compound A, or compound B were then determined, and the % by weight values of DGLA, compound A, and compound B were calculated.

Device: 6890N Network GC system (Agilent Technologies)
Column: DB-WAX, length 30 m×inside diameter 0.25 mm×film thickness 0.25 μm (Agilent Technologies)
Column temperature conditions: 2.5 minutes at 60° C.→heated at 20° C./min→180° C.→heating at 2° C./min→15 minutes at 230° C.
Inlet temperature conditions: 210° C., splitless, split vent sampling time 1.5 min, purge flow rate 40 mL/min
Injection conditions: injection volume 1 μL, sample concentration 1 mg/mL or less
Detector: FID
Detector temperature: 280° C.
Carrier gas conditions: helium, linear velocity 24 cm/min Thereafter, in the high-temperature rectification process, the following rectification was performed on 32 g of the residue excluding the initial distillates obtained in the low-temperature rectification process. A fractioning column with a vacuum jacket (Kiriyama Glass) was used as a fractioning column, and two Sulzer Lab Packing EX units (Sulzer Chemtech) were used for internal packing. The diameter of the fractioning column with a vacuum jacket was 25 mm, and the size of each Sulzer Lab Packing EX unit was 25 mm×50 mm. Rectification was performed with a liquid temperature inside the column base oven, that is, the column bottom temperature, of 195° C., a column top vapor temperature, that is, the column top temperature, of 150° C., and a pressure in front of the vacuum pump, that is, the minimum pressure in the distillation column; i.e. the degree of vacuum, of 30 Pa. In the high-temperature rectification process, fractions of C22 and larger were removed as a residue, that is, a residual fraction, and 19 g of a main distillate was obtained. DGLA was further concentrated in the main distillate.

The obtained main distillate was used in HPLC under the following conditions to fractionate a DGLA eluted fraction. The DGLA eluted fraction corresponds to a concentrated microbial oil.

The amounts of fatty acids contained and the fatty acid composition were found for the obtained main distillate after the high-temperature rectification process and the DGLA eluted fraction using gas chromatography (GC) in the same manner as in Comparative Example 1, and the DGLA content, that is, the content of DGLA with respect to the obtained fraction, and the recovery rate were further calculated. The results are shown in Table 2 as well as in Table 3. As shown in Table 2, the DGLA content in the main distillation fraction after the high-temperature rectification process was 91.9% by weight; the DGLA content in the DGLA eluted fraction was 96.4% by weight; and the DGLA recovery rate was 100.0%, indicating that DGLA was obtained with very high purification efficiency.

HPLC Conditions
Column: YMC pack ODS-AQ-HG 20 mm φ×500 mm (YMC Co., Ltd.)
Pump: 1200 Series G1361A Prep Pump (Agilent Technologies)
Column temperature: around 21° C.
Mobile phase: 17.5 mL/min of methanol
Sample conditions: load 2.4 g, that is, the material load factor is 3% by weight with respect to an adsorbent.

Working Example 2

The starting material ethyl ester 2 used in Working Example 1 was used as a sample in a rectification including the following low-temperature rectification process and high-temperature rectification process.

In the low-temperature rectification process, the following rectification was performed on 100 g of the starting material ethyl ester 2. A fractioning column with a vacuum jacket (Kiriyama Glass) was used as a fractioning column, and two Sulzer Lab Packing EX units (Sulzer Chemtech) were used for internal packing. The diameter of the fractioning column with a vacuum jacket was 25 mm, and the size of each Sulzer Lab Packing EX unit was 25 mm×50 mm. Rectification was performed with a liquid temperature inside the column base oven, that is, the column bottom temperature, of 180° C., a column top vapor temperature, that is, the column top temperature, of 140° C., and a pressure in front of the vacuum pump, that is, the minimum pressure in the distillation column; i.e. the degree of vacuum, of 20 Pa. In the low-temperature rectification process, fractions of C18 and smaller were removed as initial distillates, and 48 g of a residue excluding the initial distillates was obtained. When the amounts of fatty acids and the fatty acid composition were confirmed for the residue excluding the initial distillates using the same gas chromatography as in Comparative Example 1, DGLA was contained in a concentrated state in the residue excluding the initial distillates. In addition, the contents of compound A and compound B appearing in a chromatogram of the residue excluding the initial distillates are shown in Table 2.

Thereafter, in the high-temperature rectification process, the following rectification was performed on 45 g of the residue excluding the initial distillates obtained in the low-temperature rectification process. A fractioning column with a vacuum jacket (Kiriyama Glass) was used as a fractioning column, and two Sulzer Lab Packing EX units (Sulzer Chemtech) were used for internal packing. The diameter of the fractioning column with a vacuum jacket was 25 mm, and the size of each Sulzer Lab Packing EX unit was 25 mm×50 mm. Rectification was performed with a liquid temperature inside the column base oven, that is, the column bottom temperature, of 185° C., a column top vapor temperature, that is, the column top temperature, of 145° C., and a pressure in front of the vacuum pump, that is, the minimum pressure in the distillation column; i.e. the degree of vacuum, of 20 Pa. In the second rectification process, fractions of C22 and larger were removed as a residue, that is, a residual fraction, and 28 g of a main distillate was obtained. It is presumed that DGLA is further concentrated in the main distillate.

The obtained main distillate was used in HPLC under the following conditions to fractionate a DGLA eluted fraction. The DGLA eluted fraction corresponds to a concentrated microbial oil.

The amounts of fatty acids contained and the fatty acid composition were found for the obtained main distillate after the high-temperature rectification process and the DGLA eluted fraction using gas chromatography (GC) in the same manner as in Comparative Example 1, and the DGLA content, that is, the content of DGLA with respect to the obtained fraction, and the recovery rate were further calculated. The results are shown in Table 2 as well as in Table 4. As shown in Table 2, the DGLA content in the main distillation fraction after the high-temperature rectification process was 75.0% by weight; the DGLA content in the DGLA eluted fraction was 95.1% by weight; and the DGLA recovery rate was 61.7%, indicating that DGLA was obtained with very high purification efficiency.

In addition, as in Working Example 1, a compound A indicated by peak A and a compound B indicated by peak B appeared in a chromatogram of the main distillate (see Table 4). These compounds A and B were considered to be thermally-produced fatty acids formed by distillation treatment. The contents of compound A and compound B are shown in Tables 2 and 4. The contents in Table 4 represent contents based on the fatty acid compositions.

HPLC Conditions
Column: YMC pack ODS-AQ-HG 20 mm φ×1000 mm (YMC Co., Ltd.). Two columns with a column length of 500 mm were connected in series.
Pump: 1200 Series G1361A Prep Pump (Agilent Technologies)
Column temperature: around 21° C.
Mobile phase: 12 mL/min of methanol
Sample conditions: load 2.4 g, that is, the material load factor is 1.5% by weight with respect to an adsorbent.

TABLE 2

|  |  | Comparative Example 1 | Comparative Example 2 | Working Example 1 | Working Example 2 |
|---|---|---|---|---|---|
| Microbial oil | DGLA content (% by weight) | 37.2 | 40.9 | 91.9 | 75.0 |
|  | Ratio of C18:1 with respect to DGLA (weight ratio × 100) | 23.5 | 10.3 | 0.2 | 7.6 |
|  | Ratio of C18:2 with respect to DGLA (weight ratio × 100) | 17.8 | 7.4 | 0.1 | 4.2 |
|  | Total ratio of C18:1 + C18:2 with respect to DGLA (weight ratio × 100) | 41.3 | 17.7 | 0.3 | 11.8 |
|  | Ratio of C18:0 with respect to DGLA (weight ratio × 100) | 2.7 | 11.2 | 1.4 | 7.9 |
|  | Ratio of C22:0 with respect to DGLA (weight ratio × 100) | 8.4 | 17.0 | 0.1 | 0.7 |
|  | Ratio of C24:0 with respect to DGLA (weight ratio × 100) | 26.1 | 57.3 | 0.0 | 0.0 |
|  | Ratio of C22:0 + C24:0 with respect to DGLA (weight ratio × 100) | 34.5 | 74.3 | 0.1 | 0.7 |
|  | Content of compound A (% by weight) | — | — | 0.5 | 0.5 |
|  | Content of compound B (% by weight) | — | — | 0.5 | 0.5 |
| DGLA eluted fraction | DGLA content (wt. %) | 91.1 | 94.4 | 96.2 | 95.1 |
|  | DGLA recovery rate | 8.1% | 5.1% | 100.0% | 61.7% |

TABLE 3

| | After low-temperature rectification | After high-temperature rectification |
|---|---|---|
| | Fraction | |
| Composition | Residue excluding initial distillates | Fraction 1-3 excluding main distillates |
| C18:0 | 0.8% | 1.3% |
| C18:1n-9 | 0.1% | 0.2% |
| C18:1n-7 | 0.0% | 0.0% |
| C18:2n-6 | 0.0% | 0.1% |
| C18:3n-6 | 0.0% | 0.0% |
| C18:3n-3 | 0.0% | 0.0% |
| C18:4n-3 | 0.0% | 0.0% |
| C20:2 | 0.8% | 1.1% |
| C20:3n-6 | 62.7% | 91.9% |
| compound A | 0.2% | 0.5% |
| compound B | 0.2% | 0.5% |
| C20:4n-6 | 0.4% | 0.6% |
| C20:3n-3 | 0.1% | 0.1% |
| C20:4n-3 | 0.3% | 0.5% |
| C22:0 | 6.4% | 0.1% |
| C22:3 | 1.0% | 0.1% |
| C24:0 | 19.7% | 0.0% |
| others | balance | balance |

TABLE 4

| | After low-temperature rectification | After high-temperature rectification |
|---|---|---|
| | Fraction | |
| Composition | Residue excluding initial distillates | Fraction 1-4 excluding main distillates |
| C18:0 | 4.3% | 6.4% |
| C18:1n-9 | 3.9% | 5.8% |
| C18:1n-7 | 0.2% | 0.3% |
| C18:2n-6 | 2.2% | 3.3% |
| C18:3n-6 | 0.7% | 1.0% |
| C18:3n-3 | 0.1% | 0.2% |
| C18:4n-3 | 0.0% | 0.0% |
| C20:0 | 1.6% | 2.0% |
| C20:1 | 0.8% | 1.1% |
| C20:2 | 0.7% | 1.0% |
| C20:3n-6 | 52.5% | 75.0% |
| compound A | 0.2% | 0.5% |
| compound B | 0.2% | 0.5% |
| C20:4n-6 | 0.3% | 0.5% |
| C20:3n-3 | 0.0% | 0.1% |
| C20:4n-3 | 0.3% | 0.4% |
| C22:0 | 6.4% | 0.5% |
| C22:3 | 1.0% | 0.4% |
| C24:0 | 19.8% | 0.0% |
| others | balance | balance |

As shown in Tables 2 to 4, it was found that a microbial oil having a DGLA content of 50% by weight or greater due to rectification and containing at least 0.0001% by weight of thermally-produced fatty acids is very useful for obtaining DGLA using reverse phase column chromatography from the perspective of efficiently obtaining a high-concentration DGLA. Such a microbial oil can be obtained by a production method comprising a rectification process performed under specific conditions or a production method comprising a rectification process using a distillation column containing structured packing.

In this way, with the present invention, it is possible to efficiently obtain a microbial oil containing DGLA at a high content and to efficiently obtain a concentrated microbial oil containing DGLA at a high content.

Accordingly, with the present invention, it is possible to efficiently provide a microbial oil and a concentrated microbial oil containing a target LC-PUFA at a high content, and to provide a production method useful for efficiently obtaining such a microbial oil and a concentrated microbial oil as well as various applications of the microbial oil and the concentrated microbial oil.

The disclosure of Japanese Patent Application No. 2013-251401, filed Dec. 4, 2014, is incorporated herein by reference in its entirety.

All publications, patent applications, and technical standards mentioned in this specification are herein incorporated by reference to the same extent as if each individual publication, patent application, or technical standard was specifically and individually indicated to be incorporated by reference.

The invention claimed is:

1. A microbial oil comprising:
    arachidonic acid (ARA) or Mead acid in a fatty acid alkyl ester form or in a free fatty acid form at a content of at least 50% by weight of the total weight of fatty acids in the microbial oil; and
    one or more trans isomers of ARA or Mead acid at a total content of 0.0001% to 3.0% by weight of the total weight of fatty acids in the microbial oil,
    wherein the microbial oil comprises a mixture of fatty acid alkyl esters or free fatty acids obtained by the steps of i) performing hydrolysis or alkyl esterification of a crude oil obtained from a microbial biomass from a microorganism capable of producing ARA or Mead acid to produce a hydrolyzed or esterified crude oil; and ii) purifying the hydrolyzed or esterified crude oil by rectification using a distillation column containing a structured packing, under conditions including a column bottom temperature of 160° C. to 230° C. and a minimum pressure in a distillation column of 0.1 Pa to 30 Pa,
    wherein the one or more trans isomers of ARA or Mead acid are generated during the rectification step as thermally-produced fatty acids.

2. The microbial oil according to claim 1, wherein the content of ARA or Mead acid is 80% to 98% by weight of the total weight of fatty acids in the microbial oil.

3. The microbial oil according to claim 1, wherein the total content of the one or more trans isomers of ARA or Mead acid is 0.001% to 3.0% by weight of the total weight of fatty acids in the microbial oil.

4. The microbial oil according to claim 1, further comprising a saturated fatty acid having 22 or 24 carbon atoms, wherein the total content of the saturated fatty acid having 22 carbon atoms and the saturated fatty acid having 24 carbon atoms is i) at most 6.0% by weight of the total weight of fatty acids in the microbial oil, or ii) at most 10/100 (weight ratio) of the content of ARA or Mead acid.

5. The microbial oil according to claim 1, further comprising a saturated fatty acid having 24 carbon atoms, wherein the content of the saturated fatty acid having 24 carbon atoms is i) at most 3.0% by weight of the total weight of fatty acids in the microbial oil, or ii) at most 4/100 (weight ratio) of the content of ARA or Mead acid.

6. The microbial oil according to claim 1, further comprising one or more fatty acids having a partition number of 12 to 16 and having a number of carbon atoms other than 20, wherein the content of the one or more fatty acids having a partition number of 12 to 16 and having a number of carbon atoms other than 20 is i) at most 10.0% by weight of the total weight of fatty acids in the microbial oil, or ii) at most 15/100 (weight ratio) of the content of ARA or Mead acid.

7. The microbial oil according to claim 6, wherein the one or more fatty acids having a partition number in the range of 12 to 16 and having a number of carbon atoms other than 20 are selected from the group consisting of a saturated fatty acid having 18 carbon atoms, a monounsaturated fatty acid having 18 carbon atoms, a diunsaturated fatty acid having 18 carbon atoms, a triunsaturated fatty acid having 18 carbon atoms, and a tetraunsaturated fatty acid having 18 carbon atoms.

8. The microbial oil according to claim 7, wherein the content of the monounsaturated fatty acid having 18 carbon atoms is i) at most 7.0% by weight of the total weight of fatty acids in the microbial oil, or ii) at most 10/100 (weight ratio) of the content of ARA or Mead acid.

9. The microbial oil according to claim 7, wherein the content of the diunsaturated fatty acid having 18 carbon atoms is at most 7/100 (weight ratio) of the content of ARA or Mead acid.

10. The microbial oil according to claim 7, wherein the total content of the monounsaturated fatty acid having 18 carbon atoms and the diunsaturated fatty acid having 18 carbon atoms is at most 15/100 (weight ratio) of the content of ARA or Mead acid.

11. The microbial oil according to claim 7, wherein the content of the saturated fatty acid having 18 carbon atoms is at most 11/100 (weight ratio) of the content of ARA or Mead acid.

12. A production method for obtaining the microbial oil according to claim 1, comprising the steps of:
    (a) providing a starting oil containing ARA or Mead acid in an alkyl ester form or in a free fatty acid form, obtained from a microbial biomass from a microorganism capable of producing ARA or Mead acid; and
    (b) (i) purifying the starting oil by rectification under conditions including a column bottom temperature of 160° C. to 230° C. and a minimum pressure in a distillation column of 0.1 Pa to 30 Pa, thereby obtaining the microbial oil; or
    (ii) performing rectification on the starting oil using a distillation column containing a structured packing under conditions including a column bottom temperature of 160° C. to 230° C. and a minimum pressure in the distillation column of 0.1 Pa to 30 Pa, thereby obtaining the microbial oil.

13. The production method according to claim 12, wherein step (b) comprises a plurality of rectification cycles under mutually differing conditions for the column bottom temperature and the minimum pressure in the distillation column.

14. The production method according to claim 13, wherein the rectification step comprises a low-temperature rectification at a column bottom temperature of 160° C. to 220° C. and a minimum pressure in the distillation column of 0.1 Pa to 30 Pa; and a high-temperature rectification at a column bottom temperature of 170° C. to 230° C. and a minimum pressure in the distillation column of 0.1 Pa to 30 Pa, and wherein the column bottom temperature in the high-temperature rectification is 3° C. to 20° C. higher than the column bottom temperature of the low-temperature rectification.

15. The production method according to claim 12, wherein the structured packing of step (b) (ii) has a specific surface area per unit of 125 $m^2/m^3$ to 1700 $m^2/m^3$.

16. The microbial oil of claim 1, wherein the microbial oil is a concentrated microbial oil, comprising:
    a content of ARA or Mead acid, in a fatty acid alkyl ester form or in a free fatty acid form, of 90% to 98% by weight of the total weight of fatty acids in the concentrated microbial oil;
    a total content of a saturated fatty acid having 24 carbon atoms and a saturated fatty acid having 22 carbon atoms of at most 1.0% by weight of the total weight of fatty acids in the concentrated oil; and
    a content of a monounsaturated fatty acid having 18 carbon atoms of at most 5.0% by weight of the total weight of fatty acids in the concentrated oil.

17. A production method for obtaining a concentrated microbial oil, comprising:
    obtaining a microbial oil containing ARA or Mead acid in a fatty acid alkyl ester form or in a free fatty acid form using the production method according to claim 12; and concentrating the obtained microbial oil using reverse phase column chromatography, thereby obtaining the concentrated microbial oil.

18. A supplement, a medicament, a cosmetic, or an animal food, each comprising the microbial oil according to claim 1.

19. A supplement, a medicament, a cosmetic, or an animal food, each comprising the concentrated microbial oil obtained by the production method of claim 17.

20. A medicament comprising the microbial oil according to claim 1.

* * * * *